United States Patent [19]
Whitten et al.

[11] Patent Number: 5,959,109
[45] Date of Patent: *Sep. 28, 1999

[54] COMPOUNDS AND METHODS FOR INCREASING ENDOGENOUS LEVELS OF CORTICOTROPIN-RELEASING FACTOR

[75] Inventors: Jeffrey P. Whitten, San Diego; James R. McCarthy, Solona Beach; Zhengyu Liu, San Diego; Charles Q. Huang, San Diego; Philip E. Erickson, San Diego; Dominic P. Behan, San Diego, all of Calif.

[73] Assignee: Neurocrine Biosciences, Inc., San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/645,637

[22] Filed: May 15, 1996

[51] Int. Cl.⁶ .................................................. C07D 239/02
[52] U.S. Cl. .......................... 544/311; 544/298; 544/309; 544/242
[58] Field of Search ................................... 544/298, 309, 544/311, 242

[56] References Cited

U.S. PATENT DOCUMENTS

3,930,006  12/1975  Wiggins et al. .......................... 424/254

FOREIGN PATENT DOCUMENTS

| 2758115 | 12/1977 | Germany . |
| 51-009122 | 1/1976 | Japan . |
| 51-140926 | 12/1976 | Japan . |
| 2-179624 | 7/1990 | Japan . |
| 8-179455 | 7/1996 | Japan . |
| WO 96/02569 | 2/1996 | WIPO . |

OTHER PUBLICATIONS

Ando et al., CA 86:107999, (Print out of CAS Online search), JP 51140926.

Ando et al., CA 84:166238, (Print out of CAS Online search), JP 51009122.

Mikitenko et al., CA 102:24575, (Print out of CAS Online search), Khim. Getrotsikl. Soedin. (1984), (8), 1126–8.

Wiley et al., J. Med. Chem., vol. 6, pp. 333–334, (1963).

Ahluwalia et al., "A novel one–pot facile synthesis of 1,3,–diaryl–6–ethoxycarbonyl–1,2,3,4–tetrahydro–4,7–dioxo–2–thioxo–7H–pyrona[2,3–d]pyrimidines," *Indian Journal of Chemistry 35B*: 1319–1321, 1996.

Ahluwalia et al., "Synthesis of some new 1,3,–diaryl–5–(2,3–dihydrobenzothiazol–2–ylidene)–2–thiobarbituric acids," *Indian Journal of Chemistry 33B*: 1089–1090, 1994.

Ahluwalia et al., "Synthesis of some new substituted 1,3,–diaryl–6–cyano–7–imino–7H–pyrano[2,3–d]pyrimidines," *Indian Journal of Chemistry 32B*: 1272–1274, 1993.

(List continued on next page.)

*Primary Examiner*—S. Mark Clardy
*Assistant Examiner*—Sabiha N. Qazi
*Attorney, Agent, or Firm*—Seed and Berry LLP

[57] ABSTRACT

Ligand inhibitors for increasing levels of free corticotropin-releasing factor (CRF) in the brain. Such ligand inhibitors cause release of CRF from the CRF/CRF-binding protein complex. Administration of the ligand inhibitors provide improvement in learning and memory, result in decreased food intake and/or provide treatment for diseases associated with low levels of CRF in the brain, notably Alzheimer's disease. The ligand inhibitor is represented by the formula:

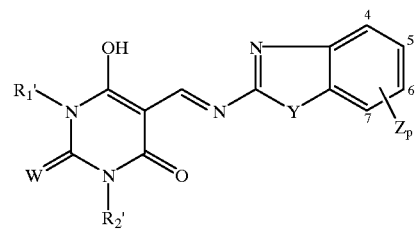

18 Claims, 4 Drawing Sheets

OTHER PUBLICATIONS

Clark–Lewis and Thompson, "5–Aminomethylene–1: 3–dimethylbarbituric Acids," *Journal of the Chemical Society*, No. III, pp. 2401–2408, 1959.

Eiden and Iwan, "Reaktionen von 1–Phenyl–1–cyan–2–aminoäthen mit substituierten Acetaldehyden," *Archiv der Pharmazie 304*(8): 628–633, 1971. (+Chemical Abstract No. 75:151493).

Hirota et al., "Novel Intramolecular Rearrangement of 5–Carbamoyluracils into Barbituric Acids," *Tetrahedron 46*(10): 3431–3438, 1990.

Koyama and Kozuka, "Murexide Reaction of Caffeine with Hydrogen Peroxide and Hydrochloric Acid. II," *J. Heterocyclic Chem. 27:* 667–671, 1990.

Kumar et al., "Sustituted Thiobarbituric Acids as Antiparkinsonian Agents," *Indian Journal of Chemistry 22B:* 955–958, 1983.

Mikitenko and Romanov, "Condensed heterocycles with a thiozole nucleus. 8. Thiazolo[3,4–a]pyrimido[5,4–e]pyrimidines," *Chemical Abstracts Online,* Abstract No. 102:24575, 1985. See Also *Khim. Geterotsikl. Soedin* (8): 126–1128, 1984.

Nightingale and Alexander, "Some Nitrogen Substituted Barbituric Acids and their Derivatives," *Journal of the American Chemical Society 58:* 794–796, 1936.

Nightingale and Taylor, "Phenyl Alkyl Nitrogen Substitution and Reactivity in the Barbituric Acid Series," *Journal of the American Chemical Society 61:* 1015–1017, 1939.

Pestov, D., "A New Synthetic Route to 5–Aminomethylene Derivatives of Barbituric Acids," *Mendeleev Commun.* (1): 14, 1994.

Ridi and Checchi, "Nuovi derivati antipirinici, iso–antipirinici, pirazolidinici," *Annali di Chimica XLIII:* 816–826, 1953. (+ Chemical Abstract, Column 6234, Section d).

Sakellariou et al., "Preparation of a New Series, The 3–Ureidomethylenecoumarins By Condensation of 4–Hydroxycoumarin With Substituted Ureas," *Synthetic Communications 20*(22): 3443–3451, 1990.

Schmidt et al., "Novel Barbituric Acid Derivatives, Uracil–Pyridinium Salts and Polycondensed Oxopyrimidines," *Heterocycles 43*(10): 2153–2167, 1996.

Tomkins et al., "BTS 71 412: In Vitro Profile of a Novel Pyrazlinone Immunosuppressant," *Int. J. Immunopharmac. 17:* 357–364, 1995.

Van Tinh et al., "Ring Closure Reactions of Cyclic 2–Arylaminomehtylene 1,3–diones," *Journal Heterocyclic Chem. 33:* 905–910, 1996.

Wiley et al., "Hydroxypyrimidine–5–carboxaldehyde Derivatives in Cancer Chemotherapy," *Journal Medicinal Chemistry* (3): 333–334, 1963.

Wipfler et al., "Zur Reaktivität von C = N–Doppelbindungssystemen, XV Die Reaktion von Anilinomethylen–barbitursäuren mit methylenaktiven Nitrilen," *Z. Naturforsch 33b:* 1016–1019, 1978. (+ Chemical Abstract No. 90:186885).

Chalmers et al., "Corticotrophin–releasing factor receptors: from molecular biology to drug design," *Trends in Pharmacological Science 17*(4): 166–172, 1996.

COMPOUNDS AND METHODS FOR INCREASING ENDOGENOUS LEVELS OF CORTICOTROPIN-RELEASING FACTOR

TECHNICAL FIELD

The present invention relates generally to compounds and methods for increasing endogenous levels of neuropeptides and, more specifically, to increasing corticotropin-releasing factor levels in the brain.

BACKGROUND OF THE INVENTION

Recent clinical data have implicated corticotropin-releasing factor ("CRF") in neuropsychiatric disorders and in neurodegenerative diseases, such as Alzeimer's disease. Alzheimer's disease is a neurodegenerative brain disorder which leads to progressive memory loss and dementia. By current estimates, over two million individuals in the United States suffer from this disease. In particular, several lines of evidence have implicated CRF in Alzheimer's disease (AD) (Behan et al., *Nature* 378(16):284, 1995). First, there are dramatic (greater than 50%) decreases in CRF (Bissette et al., *JAMA* 254:3067, 1985; DeSouza et al., *Brain Research* 397:401, 1986; Whitehouse et al., *Neurology* 37:905, 1987; DeSouza, *Hospital Practice* 23:59, 1988; Nemeroff et al., *Regul. Peptides* 25:123, 1989) and reciprocal increases in CRF receptors (DeSouza et al., 1986; DeSouza, 1988) in cerebrocortical areas that are affected in AD, while neither CRF nor CRF receptors are quantitatively changed in non-affected areas of the cortex (DeSouza et al., 1986). Second, chemical affinity crosslinking studies indicate that the increased CRF receptor population in cerebral cortex in AD have normal biochemical properties (Grigoriadis et al., *Neuropharmacology* 28:761, 1989). Additionally, observations of decreased concentrations of CRF in the cerebrospinal fluid (Mouradian et al., *Neural Peptides* 8:393, 1986; May et al., *Neurology* 37:535, 1987) are significantly correlated with the global neuropsychological impairment ratings, suggesting that greater cognitive impairment is associated with lower CRF concentrations in cerebrospinal fluid (Pomara et al., *Biological Psychiatry* 6:500, 1989).

Available therapies for the treatment of dementia are severely limited. Tacrine™, a recently approved drug, leads to only marginal memory improvement in Alzheimer's patients, and has the undesirable side effect of elevating liver enzymes.

Alterations in brain CRF content have also been found in Parkinson's disease and progressive supranuclear palsy, neurological disorders that share certain clinical and pathological features with AD. In cases of Parkinson's disease, CRF content is decreased and shows a staining pattern similar to cases of AD (Whitehouse et al., 1987; DeSouza, 1988). In progressive supranuclear palsy, CRF is decreased to approximately 50% of control values in frontal, temporal, and occipital lobes (Whitehouse et al., 1987; DeSouza, 1988).

Some depressive disorders are also associated with decreased levels of CRF. Patients in the depressive state of seasonal depression and in the period of fatigue in chronic fatigue syndrome demonstrate lower levels of CRF in the cerebrospinal fluid (Vanderpool et al., *J Clin. Endocrinol. Metab.* 73:1224, 1991).

Although some depressions have a high improvement rate and many are eventually self-limiting, there are major differences in the rate at which patients recover. A major goal of therapy is to decrease the intensity of symptoms and hasten the rate of recovery for this type of depression, as well as preventing relapse and recurrence. Anti-depressants are typically administered, but severe side effects may result (e.g., suicidality with fluoxetine, convulsions with bupropion). (See Klerman et al. in *Clinical Evaluation of Psychotropic Drugs: Principles and Guidelines*, R. F. Prien and D. S. Robinson (eds.), Raven Press, Ltd. N.Y., 1994, p. 281.)

Hypoactivation of the stress system as manifested by low CRF levels may play a role in other disorders as well. For examples, some forms of obesity are characterized by a hypoactive hypothalamic-pituitary-adrenal axis (Kopelman et al., *Clin. Endocrinol* (Oxford) 28:15, 1988; Bernini et al., *Horm. Res.* 31:133, 1989), some patients with post-traumatic stress syndrome have low cortisol excretion (Mason et al., *J. Neu. Men. Dis.* 174:145, 1986), and patients undergoing withdrawal from smoking have decreased excretion of adrenaline and noradrenaline, as well as decreased amounts of cortisol in blood (West et al., *Psychopharmacology* 84:141, 1984; Puddy et al., *Clin. Exp. Pharmacol. Physiol.* 11:423, 1984). These manifestations all point to a central role for CRF in these disorders because CRF is the major regulator of the hypothalamic-pituitary-adrenal axis.

Treatments for these disorders have poor efficacy. For example, the most effective approach to treatment of obesity is a behavior-change program. However, few participants reach goal weight and the relapse rate is high (see Halmi et al. in *Clinical Evaluation of Psychotropic Drugs: Principles and Guidelines*, R. F. Prien and D. S. Robinson (eds.), Raven Press, Ltd. New York, 1994, p. 547).

In view of the deficiencies in treatments for such disorders and diseases, more effective treatments are needed. The present invention exploits the correlation of reduced levels of CRF with various neuro-physiologically based disorders and diseases to effectively treat such diseases by increasing levels of free CRF, and further provides other related advantages.

SUMMARY OF THE INVENTION

The present invention provides ligand inhibitors and methods for increasing the level of free CRF in the brain by administering to a patient an effective amount of a ligand inhibitor of a CRF/CRF-binding protein ("CRF/CRF-BP") complex. Administration of the ligand inhibitor causes release of CRF from the CRF/CRF-BP complex. Therapeutic compositions are also provided which comprise a ligand inhibitor in combination with a physiologically acceptable carrier or diluent.

In short, it has been found that certain ligand inhibitors having a high affinity to human CRF-binding protein ("CRF-BP") can be administered which will effectively compete with human CRF in the formation of the CRF/CRF-BP complexes. In this manner, such ligand inhibitors increase the effective in vivo concentration in a mammal of endogenous CRF (and/or the effective concentration of a CRF agonist or CRF antagonist optionally administered along with such ligand inhibitors) for the purpose of achieving a particular therapeutic purpose. In other words these ligand inhibitors serve to block the effect of CRF-BP and thus to increase the concentration of endogenous CRF in those regions of the body where CRF-BP is present.

More specifically, the ligand inhibitors of this invention have a high affinity to CRF-BP, but themselves exhibit relatively little propensity to bind to the CRF receptor. As a result, such ligand inhibitors can be administered to prevent the clearance of endogenous CRF from particular regions and thereby stimulate the biological effect of CRF in vivo, and in certain instances, it may be advantageous to administer such ligand inhibitors along with CRF or a CRF agonist. The very nature of these ligand inhibitors is such that potentially undesirable side effects are minimized or totally obviated. They may also be administered along with CRF antagonists to prevent the clearance of some CRF antagonists from a target region, particularly if the CRF antagonist has a fairly high binding affinity to CRF-BP; however, the effect is counteracted to some extent by the release of endogenous CRF that would otherwise be bound to CRF-BP.

The ligand inhibitors of this invention are useful for therapeutic treatment to promote parturition in pregnancy, to stimulate the respiratory system, to combat obesity, and to counteract the effects of Alzheimer's disease and of chronic fatigue syndrome; however, for some of these indications, the agents must be administered in a manner so that they are delivered to the brain.

In the practice of this invention, the ligand inhibitor is one or more compounds having the following structure (I), (II) or (III):

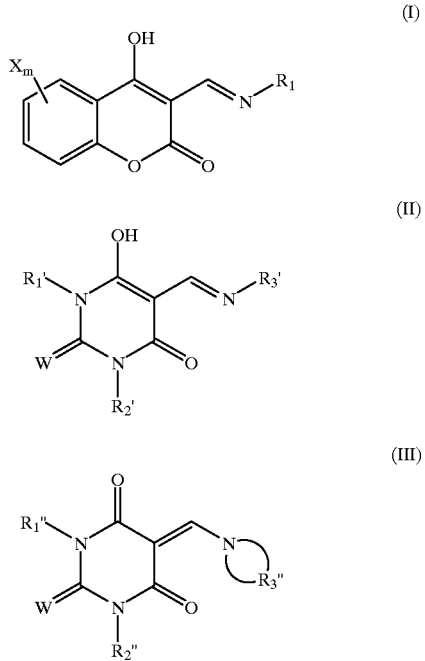

including keto tautomers, stereoisomers and pharmaceutically acceptable salts thereof, wherein $R_1$ and $X_m$ of structure (I), $R_1'$, $R_2'$, $R_3'$ and W of structure (II), and $R_1''$, $R_2''$, $R_3''$ and W of structure (III) are as disclosed below in the detailed description.

Within other aspects of the invention, methods for improving learning and memory, decreasing food intake, activating CRF neurocircuitry, treating diseases associated with low levels of CRF in the brain, treating symptoms associated with Alzheimer's disease, treating obesity, treating atypical depression, treating post-partum depression, treating age-related memory deficit, treating symptoms associated with dementia, and treating substance abuse withdrawal are provided. Within such methods, a therapeutically effective amount of a ligand inhibitor of this invention is administered to a patient as treatment for these conditions. Criteria for choosing candidates for therapy are presented, as well as methods for assessing efficacy of treatment.

Within another aspect of the invention, methods are provided for increasing the level of free CRF-related peptide by administering to a patient an effective amount of a ligand inhibitor of a CRF-related peptide/CRF-BP complex. In one embodiment, the CRF-related peptide is urocortin.

These and other aspects will become evident upon reference to the following detailed description and attached drawings.

DETAILED DESCRIPTION OF THE INVENTION

Figure 1A:
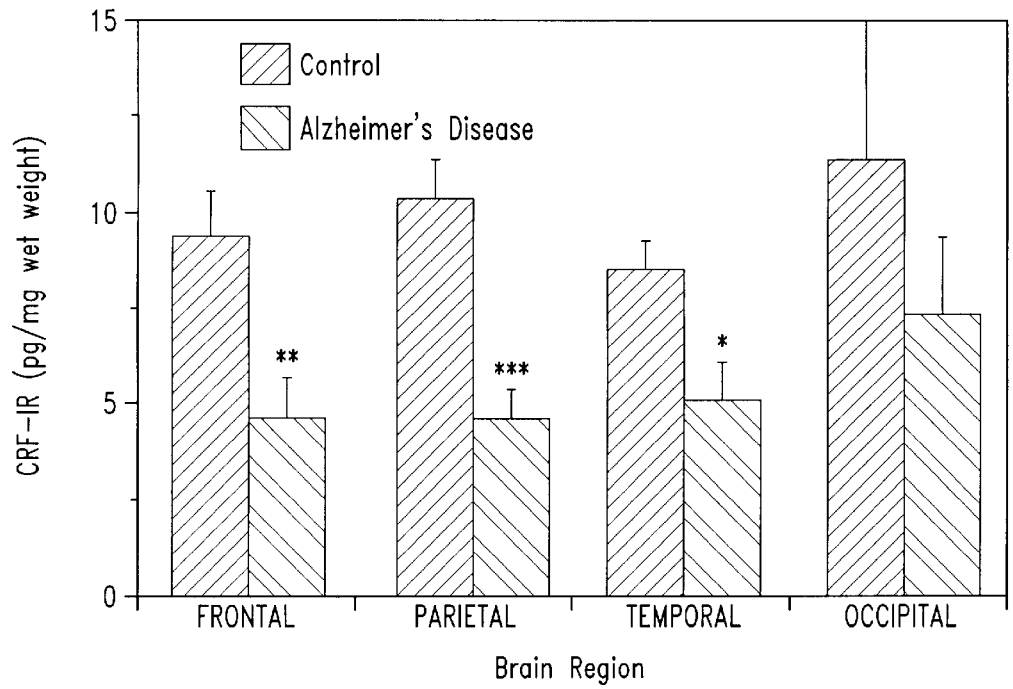
FIG. 1 is a graph showing the levels of CRF (panel A) and CRF-BP (panel B) in four areas of brain tissue taken from normal controls or Alzheimer's patients.

Prior to setting forth the invention, it may be helpful to an understanding thereof to set forth definitions of certain terms that will be used hereinafter.

"CRF" refers to a peptide that regulates the release of adrenocorticotropin (ACTH), β-endorphin, and other pro-opiomelanocortin (POMC)-derived peptides from the pituitary. In humans, rats, and other species, the amino acid sequence of CRF has been determined. The amino acid sequences of rat and human CRFs are identical and the protein is referred to as "h/rCRF." "Free CRF" refers to CRF which is not complexed or bound to CRF-binding protein or CRF receptors.

"CRF-binding protein" (CRF-BP) refers to a protein or proteins present either as a soluble factor in human plasma or associated with cell membranes and that has the ability to inhibit the function of CRF as measured by one of two methods: (1) CRF-induced ACTH release from cultured pituitary cells or from a perfused rat anterior pituitary system, or (2) CRF-induced cAMP formation from cells possessing CRF receptors or from cells which have been transfected with cloned CRF receptors. Examples of cDNA clones encoding CRF-BP have been isolated from human liver and rat brain (Potter et al., Nature 349:423, 1991).

"CRF/CRF-BP complex" refers to the complex of CRF and CRF-BP. Binding of CRF and CRF-BP may be through hydrophobic, ionic, or covalent interactions.

"Human CRF binding protein" (hCRF-BP) refers to a 37 kDa serum protein that, by specifically binding hCRF, inactivates hCRF as an ACTH secretogogue in vitro and in vivo. hCRF-BP has a high affinity for hCRF and a low affinity for oCRF, suggesting hCRF-BP may expedite the elimination of peripheral plasma hCRF. hCRF loses its ability to stimulate ACTH in vitro and in vivo when bound to hCRF-BP. The first 8 amino acids of the CRFs are believed to be involved in receptor activation while the C-terminus is primarily responsible for receptor affinity. hCRF-BP appears to prevent hCRF from stimulating corticotrophs by binding the central domain and thus preventing the ligand from interacting with the receptor and causing ACTH release.

"CRF-related peptides" refers to a peptide having 30% or greater identity to CRF and/or is active in binding to one or a combination of hCRF-BP or CRF receptors R1 and R2 (alpha and beta), or in activating the accumulation of cAMP from cells expressing CRF R1 and CRF R2 (alpha or beta). Briefly, binding to CRF receptors is assayed by incubating adherent cells transfected with the CRF receptor gene with or without unlabeled CRF-related peptide, as described in WO 95US7757, hereby incorporated by reference. Labeled r/hCRF is added (e.g., $^{125}$I-CRF) and the reaction incubated for 2 hours at room temperature. The fluid is aspirated, and the cells are washed three times with PBS. If non-adherent cells are used, the cells are washed by centrifugation. A solution of 4M guanidine thiocyanate or other solubilizer is added to the cells to solubilize the tissue. An aliquot of solubilized sample is counted. A peptide that demonstrates ≧50% inhibition at 1 μM or less is considered to be a CRF-related peptide. The accumulation of cAMP is an alternative assay. Briefly, in this assay, a peptide is added to cells expressing a CRF receptor. A 1 mM solution of isobutylmethylxanthine is also added to inhibit the breakdown of cAMP by phosphodiesterases. Cells are incubated for 1 hr at 37° C. and then washed. A solution of 95% ethanol and 20 mH HCl is added for approximately 12–18 hr at −20° C. to extract cAMP. The EtOH/HCl is removed to a tube and dried by centrifugation in vacuuo. The cAMP is reconstituted with NaOAc buffer, pH 7.5 and assayed for cAMP with a radioimmunoassay kit (Biomedical Technologies, Inc., Stoughton, Mass.) or equivalent. A peptide that demonstrates 50% maximal cAMP stimulation (as determined by stimulation with h/rCRF) at 1 μM or less is considered to be a CRF-related peptide.

Ligand Inhibitors of CRF/CRF-BP Complex

As noted above, the present invention discloses ligand inhibitors which increase the level of free CRF in the brain. Such compounds are referred to herein as ligand inhibitors due to their ability to bind the CRF/CRF-BP complex in a manner such that CRF is released from CRF-BP. The ligand inhibitor of the CRF/CRF-BP complex displaces CRF either in a reversible or irreversible fashion. Displacement may occur by causing a bound CRF molecule to become free CRF. In addition, the binding of the ligand inhibitor may inhibit binding of free CRF to CRF-BP because of a high affinity to CRF-BP, thus competing with endogenous CRF for binding to CRF-BP. Reversible or irreversible displacement of CRF may be mediated by the ligand inhibitor binding directly to the CRF binding site, or alternatively by the ligand inhibitor binding to a site that is not the CRF binding site and causing allosteric displacement of the bound CRF.

Ligand inhibitors of this invention are compounds having structure (I), (II) or (III) as identified above. While structures (I) and (II) are depicted in their enol form, it should be recognized that these structures exits in equilibrium with their keto tautomers as illustrated below:

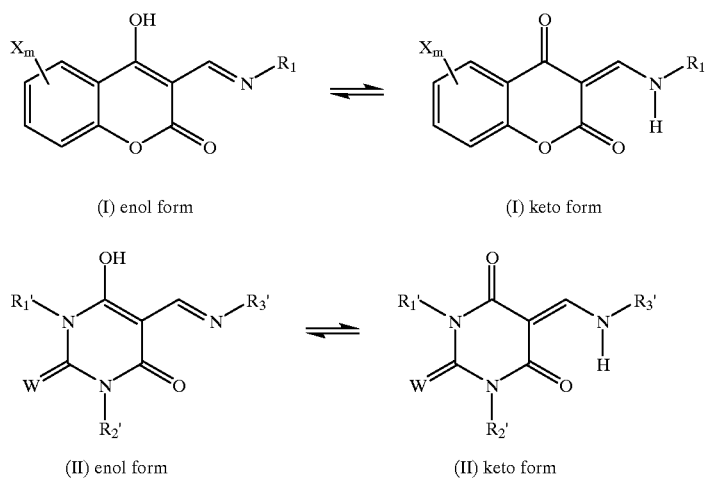

(I) enol form     (I) keto form (II) enol form     (II) keto form

Thus, both the enol and keto tautomers are included within the compounds of structures (I) and (II). Since the imine nitrogen of structure (III) is a tertiary amine, only the preferred keto form of this structure is depicted herein (although both tautomers are included within the scope of this invention).

The compounds of this invention further include stereoisomers of structures (I), (II) and (III), as well as pharmaceutically acceptable salts of the same. As substituted amino compounds, structures (I), (II) and (III) may be utilized as the free base or in the form of acid addition salts. Acid addition salts of the free base amino compounds may be prepared by methods well known in the art, and may be formed from organic and inorganic acids. Suitable organic acids include maleic, fumaric, benzoic, ascorbic, succinic, methanesulfonic, and benzenesulfonic acids. Suitable inorganic acids include hydrochloric, hydrobromic, sulfuric, phosphoric and nitric acids. The compounds of this invention also include those salts derived from inorganic bases such as sodium, potassium, lithium, ammonium, calcium, magnesium, iron, zinc, copper, manganese, aluminum salts and the like. Preferred salts are sodium, potassium, calcium and magnesium salts derived from pharmaceutically acceptable organic bases, including substituted amines.

Ligand inhibitors may also be metabolites of administered compounds. The ligand inhibitors must be accessible to the brain, either administered through the CNS or systemically. Preferably, the characteristics of the ligand inhibitor are such that it is a low affinity antagonist at the CRF receptor ($K_i \geq 1$ μM) and/or has a 100-fold selectivity to the CRF-BP ($K_i \leq 10$ nM).

In one embodiment, the ligand inhibitor is a compound having structure

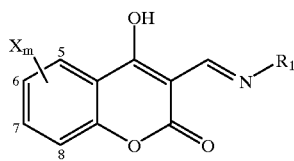

(I)

wherein

X is a substituent, m is 0, 1, 2 or 3 and represents the number of X substituents, and each occurrence of X is independently selected from halo and $C_{1-8}$alkyloxy; or $X_m$ is a phenyl moiety attached at positions 5 and 6 or 7 and 8; and $R_1$ is selected from the following structures:

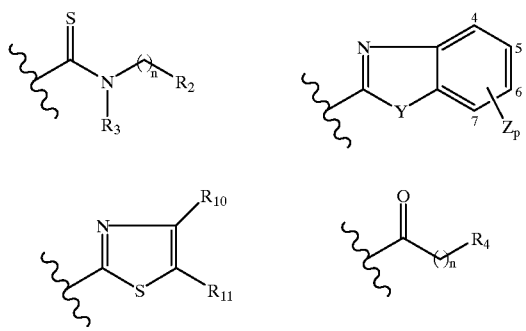

wherein n is 0, 1 or 2;

$R_2$ is selected from aryl, substituted aryl, $C_{3-8}$cycloalkyl, $C_{1-8}$alkyl, $C_{2-8}$alkenyl and $C_{2-8}$alkynyl;

$R_3$ is selected from hydrogen and methyl;

$R_4$ is selected from aryl and substituted aryl;

$R_{10}$ and $R_{11}$ are independently selected from hydrogen, halo, cyano, nitro, acetyl, $C_{1-8}$alkyl, $C_{2-8}$alkenyl, $C_{2-8}$alkynyl, $C_{1-8}$alkyloxy, $C_{3-8}$cycloalkyl, aryl, aryloxy, $C_{1-8}$haloalkyl and $C_{3-8}$cycloalkyl$C_{1-8}$alkyl;

Y is selected from S, NH and N(CH$_3$); and

Z is a substituent, p is 0, 1, 2 or 3 and represents the number of Z substituents, and each occurrence of Z is independently selected from halo, $C_{1-8}$alkyloxy, $C_{1-8}$alkyl, $C_{2-8}$alkenyl and $C_{2-8}$alkynyl.

As used above and throughout this disclosure, the following terms, unless otherwise indicated, shall be understood to have the following meanings:

"Halo" means iodo, bromo, chloro and fluoro.

"$C_{1-8}$alkyl" means a saturated aliphatic hydrocarbon which may be either straight-chain or branched-chain, and containing 1 to 8 carbon atoms. Representative examples include methyl, ethyl, n-propyl, n-butyl, n-pentyl, n-hexyl, isopropyl, sec-butyl, isobutyl, tert-butyl and the like.

"$C_{2-8}$alkenyl" means an unsaturated aliphatic hydrocarbon containing 2 to 8 carbon atoms, where at least two adjacent carbon atoms form a carbon-carbon double bond, and where the $C_{2-8}$alkenyl may be joined to the rest of the molecule through one of the carbons forming the double bond, or through one of the other carbon atoms of the $C_{2-8}$alkenyl. Representative examples include ethylenyl, propylenyl, 1-butenyl, 2-butenyl, isobutylenyl and the like.

"$C_{2-8}$alkynyl" means an unsaturated alphatic hydrocarbon containing 2 to 8 carbon atoms, where at least two adjacent carbon atoms form a carbon-carbon triple bond, and where the $C_{2-8}$alkynyl may be joined to the rest of the molecule through one of the carbons forming the triple bond, or through one of the other carbon atoms of the $C_{2-8}$alkynyl. Representative examples include propynyl, 1-butynyl, 2-butynyl and the like.

"$C_{3-8}$cycloalkyl" means a saturated cyclic hydrocarbon containing 3 to 8 carbon atoms, including cyclopropyl, cyclopentyl, cyclohexyl and the like.

"$C_{1-8}$alkyoxy" means an O-atom substituted with a $C_{1-8}$alkyl, including methoxy, ethoxy and the like.

"Aryl" means phenyl and naphthyl.

"Aryloxy" means an O-atom substituted with aryl, including phenoxy.

"$C_{1-8}$haloalkyl" means a $C_{1-8}$alkyl wherein one or more hydrogen atoms has been replaced with halo, including trifluromethyl and the like.

"$C_{3-8}$cycloalkyl$C_{1-8}$alkyl" means a $C_{1-8}$alkyl wherein one or more hydrogen atoms has been replaced with a $C_{3-8}$cycloalkyl, including cyclopropylmethyl, cyclohexylmethyl, cyclohexylethyl and the like.

"Aryl$C_{1-8}$alkyl" means a $C_{1-8}$alkyl wherein one or more hydrogen atoms has been replaced with aryl, including benzyl and the like.

"Aryl$C_{1-8}$alkyloxy" means a $C_{1-8}$alkyloxy wherein one or more hydrogen atoms has been replaced with aryl, including benzyloxy and the like.

"$C_{1-8}$alkoxy$C_{1-8}$alkyl" means a $C_{1-8}$alkyl wherein one or more hydrogen atoms has been replaced with a $C_{1-8}$alkoxy, including methyl $C_{1-8}$alkyl ether (CH$_3$O(CH$_2$)$_{1-8}$) such as methyl n-propyl ether and the like.

"$C_{1-8}$alkoxydicarbonyl" means a $C_{1-8}$alkoxy bonded through two adjacent carbonyl groups, i.e., —C(O)—C(O)—$C_{1-8}$alkoxy.

"$C_{1-12}$heteroaryl" means a cyclic or polycyclic moiety having at least one heteroatom selected from nitrogen, sulfur and oxygen in a ring position, and where one to twelve carbon atoms are present in all other ring positions, such that at least one ring containing a heteroatom is aromatic. Representative examples include benzofuran, benzothiophene, indole, benzopyrazole, coumarin, isoquinoline, pyrrole, thiophene, furan, thiazole, imidazole, pyrazole, thiazole, quinoline, pyrimidine, pyridine, pyridone, pyrazine, pryidazine, isothiazole, isoxazole, tetrazole and the like.

"$C_{1-12}$heteroaryl$C_{1-8}$alkyl" means a $C_{1-12}$heteroaryl having at least one $C_{1-8}$alkyl appended thereto, where the $C_{1-12}$heteroaryl$C_{1-8}$alkyl may be linked to the rest of the molecule through an atom of either the heteroaryl or alkyl group.

"$C_{1-12}$heteroaryl$C_{2-8}$alkenyl" means a $C_{1-12}$heteroaryl having at least one $C_{2-8}$alkenyl group either appended to the heteroaryl group or incorporated into the heteroaryl though a single carbon of the alkenyl group's carbon-carbon double bond, where the $C_{1-12}$heteroaryl$C_{2-8}$alkenyl may be joined to the rest of the molecule through an atom of either the heteroaryl or alkenyl group.

"Substituted aryl" means phenyl and napthyl with one or more substituents independently selected from halo, hydroxy, cyano, nitro, acetyl, $C_{1-8}$alky, $C_{1-8}$alkyloxy, $C_{3-8}$cycloalkyl, aryl, aryl$C_{1-8}$alkyl, aryloxy, aryl$C_{1-8}$alkyloxy, $C_{1-8}$haloalkyl and $C_{3-8}$cycloalkyl$C_{1-8}$alkyl, and wherein substituted phenyl has the following substitution positions:

"Substituted $C_{1-12}$heteroaryl, $C_{1-12}$heteroaryl$C_{2-8}$alkenyl or $C_{1-12}$heteroaryl$C_{2-8}$alkynyl" means a $C_{1-12}$heteroaryl, $C_{1-12}$heteroaryl$C_{2-8}$alkenyl or $C_{1-12}$heteroaryl$C_{2-8}$alkynyl, respectively, substituted with one or more substituents independently selected from halo, hydroxy, amido, suflhydryl, cyano, nitro, acetyl, $C_{1-8}$alkyl, $C_{1-8}$alkyloxy, $C_{3-8}$cycloalkyl, $C_{6-10}$aryl, substituted $C_{6-10}$aryl, aryl$C_{1-8}$alkyl, substituted aryl$C_{1-8}$alkyl, $C_{1-8}$alkyloxycarbonyl$C_{1-8}$alkyl, $C_{1-8}$alkyloxydicarbonyl, N(R)(R), $C_{6-10}$aryloxy and $C_{1-8}$haloalkyl.

In one aspect of this embodiment, the ligand inhibitor has structure (Ia):

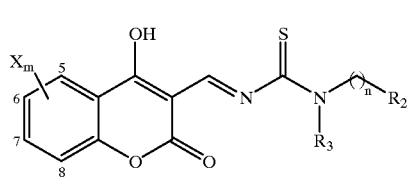

(Ia)

wherein $R_2$, $R_3$, $X_m$ and n are as defined above. Representative compounds of this embodiment are listed in Table 1. Of the compounds listed in Table 1, the following compounds have a Ki<100 nM: 1–8, 10–12, 18–21, 29 and 31–34. Compounds 1–2, 6–7, 10, 19–20 and 31–32 were found to have the lowest Ki values (i.e., <50 nM) and represent preferred embodiments.

TABLE 1

Structure (Ia)

| Cpd. No. | $R_2$ | $R_3$ | n | $X_m$ |
|---|---|---|---|---|
| 1 | 4-chlorophenyl | hydrogen | 0 | 6-chloro |
| 2 | 3,4-dichlorophenyl | hydrogen | 0 | 6-chloro |
| 3 | 4-methoxyphenyl | hydrogen | 0 | 6-chloro |
| 4 | 2,4-dichlorophenyl | hydrogen | 0 | 6-chloro |
| 5 | 4-methylphenyl | hydrogen | 0 | 6-chloro |
| 6 | 4-trifluoromethylphenyl | hydrogen | 0 | 6-chloro |
| 7 | 2,4,6-trichlorophenyl | hydrogen | 0 | 6-chloro |
| 8 | phenyl | hydrogen | 0 | 6-chloro |
| 9 | 4-phenoxyphenyl | hydrogen | 0 | 6-chloro |
| 10 | 4-cyclohexyl | hydrogen | 0 | 6-chloro |
| 11 | 4-cyanophenyl | hydrogen | 0 | 6-chloro |
| 12 | 3-nitrophenyl | hydrogen | 0 | 6-chloro |
| 13 | 1-naphthyl | hydrogen | 0 | 6-chloro |
| 14 | phenyl | hydrogen | 1 | 6-chloro |
| 15 | phenyl | hydrogen | 2 | 6-chloro |
| 16 | 4-(4'-hexyl-bicyclo [2.2.2]octanyl)phenyl | hydrogen | 0 | 6-chloro |
| 17 | 3-(3-hexyl-cyclohexyl)phenyl | hydrogen | 0 | 6-chloro |
| 18 | 2-naphthyl | hydrogen | 0 | 6-chloro |
| 19 | 4-phenylphenyl | hydrogen | 0 | 6-chloro |
| 20 | 2-phenylphenyl | hydrogen | 0 | 6-chloro |
| 21 | 4-hydroxyphenyl | hydrogen | 0 | 6-chloro |
| 22 | cyclohexyl | hydrogen | 0 | 6-chloro |
| 23 | cyclopentyl | hydrogen | 0 | 6-chloro |
| 24 | cyclopropyl | hydrogen | 0 | 6-chloro |
| 25 | 4-trifluoromethylphenyl | hydrogen | 0 | 6-fluoro |
| 26 | phenyl | methyl | 0 | 6-chloro |
| 27 | 4-acetylphenyl | hydrogen | 0 | 6-chloro |
| 28 | n-propyl | hydrogen | 0 | 6-chloro |
| 29 | 4-chlorophenyl | hydrogen | 0 | 5,6-monophenyl |
| 30 | 4-chlorophenyl | hydrogen | 0 | 7,8-monophenyl |
| 31 | 4-chlorophenyl | hydrogen | 0 | 8-chloro |
| 32 | 4-chlorophenyl | hydrogen | 0 | 6,8-dichloro |
| 33 | 4-chlorophenyl | hydrogen | 0 | 6-methoxy |
| 34 | 4-chlorophenyl | hydrogen | 0 | 7-chloro |

In another aspect of this embodiment, the ligand inhibitor has structure (Ib)

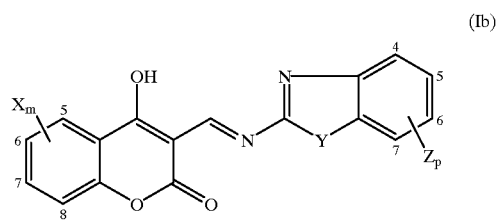

(Ib)

wherein $X_m$, Y and $Z_p$ are as defined above. Representative compounds of this embodiment are listed in Table 2. Of the compounds listed in Table 2, the following compounds have a Ki<100 nM: 35–38, 40 and 42–45. Compounds 36 and 44–45 were found to have the lowest Ki values (i.e., <50 nM) and represent preferred embodiments.

TABLE 2

Structure (b)

| Cpd. No. | Y | $X_m$ | $Z_p$ |
|---|---|---|---|
| 35 | —S— | 6-chloro | — |
| 36 | —S— | 6-chloro | 4-chloro |
| 37 | —S— | 6-chloro | 6-chloro |
| 38 | —NH— | 6-chloro | — |
| 39 | —S— | 6-chloro | 4-methyl |
| 40 | —S— | 6-chloro | 4-methoxy |
| 41 | —N(CH$_3$)— | 6-chloro | — |
| 42 | —S— | 6-fluoro | 4-chloro |
| 43 | —S— | 7-chloro | — |
| 44 | —S— | 7-chloro | 4-chloro |
| 45 | —S— | 7-chloro | 6-chloro |

In still a further aspect of this embodiment, the ligand inhibitor has structure (Ic):

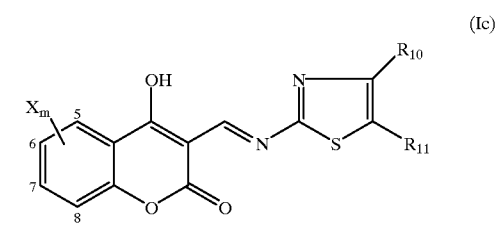

(Ic)

wherein $X_m$, $R_{10}$ and $R_{11}$ are as defined above. A representative compound of this embodiment is disclosed in Table 3.

TABLE 3

Structure (1c)

| Cpd. No. | $X_m$ | $R_{10}$ | $R_{11}$ |
|---|---|---|---|
| 46 | 6-chloro | hydrogen | hydrogen |

In yet a further aspect of this embodiment, the ligand inhibitor has structure (Id):

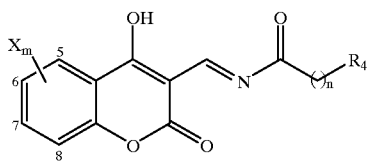

(Id)

wherein $R_4$, n and $X_m$ are as defined above. A representative compound of this embodiment is disclosed in Table 4.

TABLE 4

Structure (Id)

| Cpd. No. | $R_4$ | $X_m$ | n |
|---|---|---|---|
| 47 | phenyl | 6-chloro | 1 |

In another embodiment of this invention, the ligand inhibitor is a compound having structure (II):

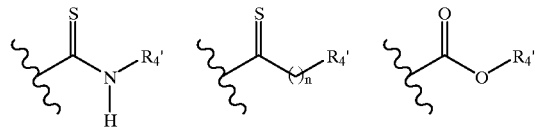

(II)

wherein

W is selected from S and O;

$R_1'$ and $R_2'$ are the same or different and independently selected from $C_{1-8}$alkyl, $C_{1-8}$alkyloxy$C_{1-8}$alkyl, aryl, substituted aryl, aryl$C_{1-8}$alkyl, substituted aryl$C_{1-8}$alkyl, $C_{3-8}$cycloalkyl, $C_{3-8}$cycloalkyl$C_{1-8}$alkyl, $C_{1-12}$heteroaryl, substituted $C_{1-12}$heteroaryl, $C_{1-12}$heteroaryl$C_{1-8}$alkyl, substituted $C_{1-12}$heteroaryl$C_{1-8}$alkyl, $C_{1-12}$heteroaryl$C_{2-8}$alkenyl and substituted $C_{1-12}$heteroaryl$C_{2-8}$alkenyl; and $R_3'$ is selected from $C_{1-12}$heteroaryl, substituted $C_{1-12}$heteroaryl, $C_{1-12}$heteroaryl$C_{1-8}$alkyl, substituted $C_{1-12}$heteroaryl$C_{1-8}$alkyl, $C_{1-12}$heteroaryl$C_{2-8}$alkenyl, substituted $C_{1-12}$heteroaryl$C_{2-8}$alkenyl and the following structures:

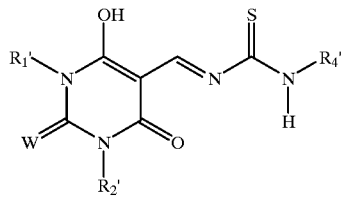

wherein n is 0, 1 or 2; and $R_4'$ is selected from aryl and substituted aryl with one or more substituents independently selected from halo and $C_{1-8}$alkyloxy.

In one embodiment, $R_3'$ is preferably selected from $C_{1-12}$heteroaryl and substituted $C_{1-12}$heteroaryl, and more preferably selected from the following structures:

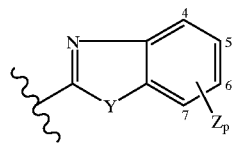

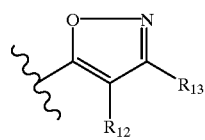

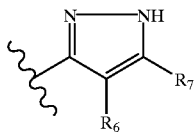

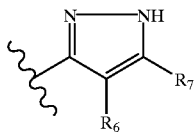

wherein n is 1 or 2;

A is selected from N and $C(R_8)$;

B is selected from N and $C(R_9)$;

Y is selected from NH, S, O and $N(CH_3)$;

Z is a substituent, p is 0, 1, 2 or 3 and represents the number of Z substituents, and each occurrence of Z is independently selected from halo, nitro, $C_{1-8}$alkyloxy, $C_{1-8}$alkyl, $C_{2-8}$alkenyl, $C_{2-8}$alkynyl and $C_{1-8}$haloalkyl;

F is a five or six membered heteroaryl ring having at least one atom selected from oxygen, nitrogen and sulfur, and optionally containing keto and N-alkyl groups;

$R_5$, $R_6$, $R_7$, $R_8$ and $R_9$ are the same or different and independently selected from hydrogen, halo, hydroxy, amido, sulfhydryl, $C_{1-8}$alkyl, $C_{2-8}$alkenyl, $C_{2-8}$alkynyl, $C_{1-8}$haloalkyl, aryl, substituted aryl, aryl$C_{1-8}$alkyl, substituted aryl$C_{1-8}$alkyl, $C_{1-8}$alkyloxycarbonyl$C_{1-8}$alkyl, $C_{1-8}$alkyloxydicarbonyl, and N(R)(R);

$R_{12}$ and $R_{13}$ are the same or different and independently selected from hydrogen, halo, amido, sulfhydryl, $C_{1-8}$alkyl, $C_{2-8}$alkenyl, $C_{2-8}$alkynyl, $C_{1-8}$haloalkyl, aryl, substituted aryl, aryl$C_{1-8}$alkyl, substituted aryl$C_{1-8}$alkyl, $C_{1-8}$alkyloxycarbonyl$C_{1-8}$alkyl and N(R)(R); and each occurrence of R is independently selected from hydrogen, $C_{1-8}$alkyl, $C_{2-8}$alkenyl, $C_{2-8}$alkynyl, aryl and aryl$C_{1-8}$alkyl.

In one embodiment of structure (II), the ligand inhibitor has structure (IIa):

(IIa)

wherein $R_1'$, $R_2'$, $R_4'$ and W are as defined above. Representative compounds of this embodiment are listed in Table 5. Of the compounds listed in Table 5, the following compounds have a Ki<100 nM: 49 and 53–54.

TABLE 5

Structure (IIa)

| Cpd. No. | W | $R_1'$ | $R_2'$ | $R_4'$ |
|---|---|---|---|---|
| 48 | S | ethyl | ethyl | 4-chlorophenyl |
| 49 | S | ethyl | ethyl | 2,4,6-trichlorophenyl |
| 50 | S | ethyl | ethyl | 4-methoxyphenyl |
| 51 | S | ethyl | ethyl | phenyl |
| 52 | S | methyl | methyl | 4-chlorophenyl |
| 53 | S | benzyl | benzyl | 4-chlorophenyl |
| 54 | S | n-propyl | n-propyl | 4-chlorophenyl |
| 55 | O | n-propyl | n-propyl | 4-chlorophenyl |
| 56 | S | phenyl | phenyl | 4-chlorophenyl |
| 57 | S | 2-phenyl-ethyl | 2-phenyl-ethyl | 4-chlorophenyl |

In another aspect of this embodiment, the ligand inhibitor has structure (IIb);

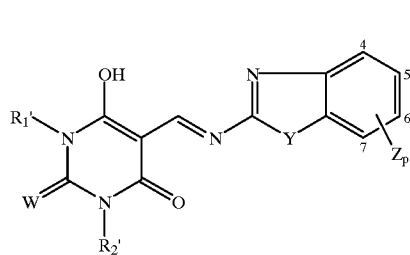

(IIb)

wherein $R_1'$, $R_2'$, Y and $Z_p$ are as defined above. Representative compounds of this embodiment are listed in Table 6. Of the compounds listed in Table 6, the following compounds have a Ki<100 nM: 58, 58-1, 66–68, 72–73, 73-1, 74–75, 75-1, 76, 76-1, 79–80, 82, 85, 85-1, 86, 86-1, 87–90, 92–95, 95-1, 97 and 97-1. Compounds 58, 73, 75–76, 82, 85, 85-1, 86, 86-1, 88–90, 92–94, 97 and 97-1 were found to have the lowest Ki values (i.e., <50 nM) and represent preferred embodiments.

TABLE 6

Structure (IIb)

| Cpd. No. | W | $R_1'$ | $R_2'$ | Y | $Z_p$ |
|---|---|---|---|---|---|
| 58 | S | ethyl | ethyl | NH | — |
| 58-1 | S | 2-phenylethyl | ethyl | NH | — |
| 59 | S | ethyl | ethyl | S | — |
| 59-1 | S | 2-phenylethyl | ethyl | S | — |
| 60 | S | ethyl | ethyl | S | 4-chloro |
| 61 | S | ethyl | ethyl | O | 5-chloro |
| 62 | S | ethyl | ethyl | N(CH$_3$) | — |
| 63 | S | phenyl | phenyl | NH | — |
| 64 | S | methyl | methyl | NH | — |
| 65 | S | methyl | methyl | S | 4-chloro |
| 66 | S | benzyl | benzyl | NH | — |
| 67 | S | benzyl | benzyl | S | 4-chloro |
| 68 | S | n-propyl | n-propyl | NH | — |
| 69 | S | n-propyl | n-propyl | S | 4-chloro |
| 70 | S | n-hexyl | n-hexyl | NH | — |
| 71 | S | n-hexyl | n-hexyl | S | 4-chloro |
| 72 | S | ethyl | ethyl | S | 4-methyl |
| 73 | S | ethyl | ethyl | S | 4-methoxy |

TABLE 6-continued

Structure (IIb)

| Cpd. No. | W | $R_1'$ | $R_2'$ | Y | $Z_p$ |
|---|---|---|---|---|---|
| 73-1 | S | 2-phenylethyl | ethyl | S | 4-methoxy |
| 74 | S | ethyl | ethyl | S | 6-chloro |
| 75 | S | ethyl | ethyl | S | 6-methyl |
| 75-1 | S | 2-phenylethyl | ethyl | S | 6-methyl |
| 76 | S | ethyl | ethyl | S | 6-methoxy |
| 76-1 | S | 2-phenylethyl | ethyl | S | 6-methoxy |
| 77 | S | ethyl | ethyl | S | 6-fluoro |
| 78 | S | ethyl | ethyl | S | 6-bromo |
| 79 | S | ethyl | ethyl | S | 6-nitro |
| 80 | S | ethyl | ethyl | S | 4-trifluoromethyl |
| 81 | S | ethyl | ethyl | S | 5,6-dimethyl |
| 82 | S | ethyl | ethyl | S | 5-nitro |
| 83 | O | n-propyl | n-propyl | NH | — |
| 84 | O | n-propyl | n-propyl | S | 4-chloro |
| 85 | S | ethyl | ethyl | NH | 5,6-dimethyl |
| 85-1 | S | 2-phenylethyl | ethyl | NH | 5,6-dimethyl |
| 86 | S | ethyl | ethyl | NH | 5-methyl |
| 86-1 | S | 2-phenylethyl | ethyl | NH | 5-methyl |
| 87 | S | ethyl | ethyl | NH | 4-methyl |
| 88 | S | ethyl | ethyl | NH | 5-chloro |
| 89 | S | ethyl | ethyl | NH | 5,6-dichloro |
| 90 | S | ethyl | ethyl | NH | 5-methoxy |
| 91 | S | —(CH$_2$)$_2$OCH$_3$ | —(CH$_2$)$_2$OCH$_3$ | NH | 5,6-dimethyl |
| 92 | S | —(CH$_2$)$_3$OCH$_3$ | —(CH$_2$)$_3$OCH$_3$ | NH | 5,6-dimethyl |
| 93 | S | 2-phenylethyl | 2-phenylethyl | S | 4-methoxy |
| 94 | S | 2-phenylethyl | 2-phenylethyl | NH | hydrogen |
| 95 | S | 2-phenylethyl | 2-phenylethyl | S | 4-chloro |
| 95-1 | S | 2-phenylethyl | ethyl | S | 4-chloro |
| 96 | S | 2-phenylethyl | 2-phenylethyl | NH | 5,6-dimethyl |
| 97 | S | 2-(2-thienyl)ethyl | 2-(2-thienyl)ethyl | NH | — |
| 97-1 | S | 3-phenylpropyl | 3-phenylpropyl | NH | — |

In a further aspect of this embodiment, the ligand inhibitor has structure (IIc):

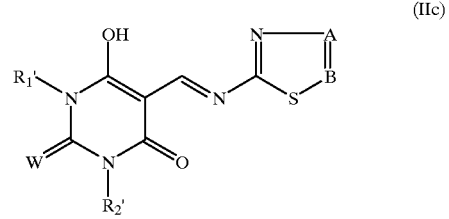

(IIc)

wherein $R_1'$, $R_2'$, W, A and B are as defined above. Depending upon the choice of A and B, structure (IIc) may have the following structures (IIc"), (IIc'), (IIc''') and (IIc""):

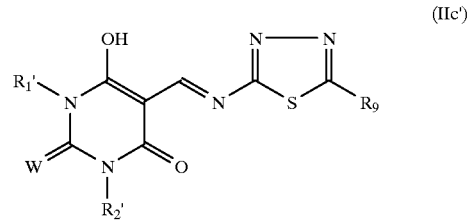

(IIc')

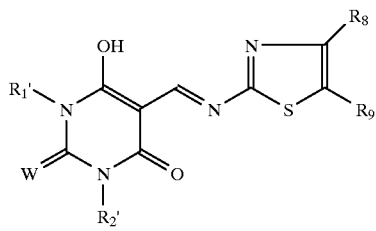
(IIc'')

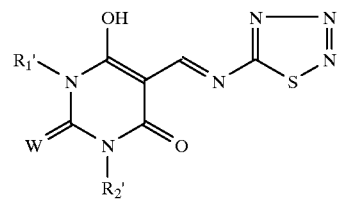
(IIc'''')

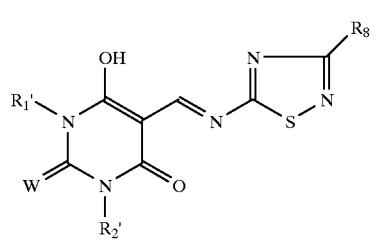
(IIc''')

wherein $R_1'$, $R_2'$, $R_8$, $R_9$ and W are as defined above. Representative compounds of this embodiment are listed in Table 7. Of the compounds listed in Table 7, the following compounds have a Ki<100 nM: 103–104, 104-1, 105–106, 110-1, 111, 115–116, 117-1, 118, 121, 131-1, 132–134, 140, 149–150, 153–157, 159–164 and 166–168. Compounds 110-1, 111, 118, 121, 131-1, 132–133, 149, 153–155, 157, 160–164 and 166–168 were found to have the lowest Ki values (i.e., <50 nM) and represent preferred embodiments.

TABLE 7

Structure (IIc)

| Cpd. No. | W | $R_1'$ | $R_2'$ | A | B | $R_8$ | $R_9$ |
|---|---|---|---|---|---|---|---|
| 98 | S | ethyl | ethyl | N | C | — | SH |
| 99 | S | benzyl | benzyl | N | C | — | SH |
| 100 | S | n-propyl | n-propyl | N | C | — | SH |
| 101 | S | ethyl | ethyl | N | C | — | methyl |
| 101-1 | S | 2-phenylethyl | ethyl | N | C | — | methyl |
| 102 | S | benzyl | benzyl | N | C | — | methyl |
| 103 | S | n-propyl | n-propyl | N | C | — | methyl |
| 104 | S | ethyl | ethyl | N | C | — | trifluoromethyl |
| 104-1 | S | 2-phenylethyl | ethyl | N | C | — | trifluoromethyl |
| 105 | S | benzyl | benzyl | N | C | — | trifluoromethyl |
| 106 | S | n-propyl | n-propyl | N | C | — | trifluoromethyl |
| 107 | S | ethyl | ethyl | C | C | —CH$_2$COOCH$_2$CH$_3$ | hydrogen |
| 108 | S | benzyl | benzyl | C | C | —CH$_2$COOCH$_2$CH$_3$ | hydrogen |
| 109 | S | n-propyl | n-propyl | C | C | —CH$_2$COOCH$_2$CH$_3$ | hydrogen |
| 110 | S | ethyl | ethyl | N | C | — | hydrogen |
| 110-1 | S | 2-phenylethyl | ethyl | N | C | — | hydrogen |
| 111 | S | benzyl | benzyl | N | C | — | hydrogen |
| 112 | S | n-propyl | n-propyl | N | C | — | hydrogen |
| 113 | S | ethyl | ethyl | C | C | —C(O)C(O)OCH$_2$CH$_3$ | hydrogen |
| 114 | S | n-propyl | n-propyl | C | C | —C(O)C(O)OCH$_2$CH$_3$ | hydrogen |
| 115 | S | benzyl | benzyl | N | C | — | —SCH$_2$CH$_3$ |
| 116 | S | n-propyl | n-propyl | N | C | — | —SCH$_2$CH$_3$ |
| 117 | S | ethyl | ethyl | C | C | hydrogen | methyl |
| 117-1 | S | 2-phenylethyl | ethyl | C | C | hydrogen | methyl |
| 118 | S | benzyl | benzyl | C | C | hydrogen | methyl |
| 119 | S | n-propyl | n-propyl | C | C | hydrogen | methyl |
| 120 | S | benzyl | benzyl | C | C | methyl | hydrogen |
| 121 | S | benzyl | benzyl | N | C | — | S—(CH$_2$)$_{15}$CH$_3$ |
| 122 | S | propyl | propyl | N | C | — | S—(CH$_2$)$_{15}$CH$_3$ |
| 123 | S | benzyl | benzyl | C | C | 3-nitrophenyl | hydrogen |
| 124 | S | propyl | propyl | C | C | 3-nitrophenyl | hydrogen |
| 125 | S | ethyl | ethyl | C | C | phenyl | hydrogen |
| 126 | S | benzyl | benzyl | C | C | phenyl | hydrogen |
| 127 | S | n-propyl | n-propyl | C | C | phenyl | hydrogen |
| 128 | S | ethyl | ethyl | C | C | t-butyl | hydrogen |
| 129 | S | benzyl | benzyl | C | C | t-butyl | hydrogen |
| 130 | S | n-propyl | n-propyl | C | C | t-butyl | hydrogen |
| 131 | S | ethyl | ethyl | C | N | —N(benzyl)(phenyl) | — |
| 131-1 | S | 2-phenylethyl | ethyl | C | N | —N(benzyl)(phenyl) | — |
| 132 | S | benzyl | benzyl | C | N | —N(benzyl)(phenyl) | — |
| 133 | S | n-propyl | n-propyl | C | N | —N(benzyl)(phenyl) | — |
| 134 | S | benzyl | benzyl | N | C | — | hydroxyl |
| 135 | S | n-propyl | n-propyl | N | C | — | hydroxyl |
| 136 | S | ethyl | ethyl | N | N | — | — |

TABLE 7-continued

Structure (IIc)

| Cpd. No. | W | R₁' | R₂' | A | B | R₈ | R₉ |
|---|---|---|---|---|---|---|---|
| 137 | S | benzyl | benzyl | N | N | — | — |
| 138 | S | n-propyl | n-propyl | N | N | — | — |
| 139 | S | ethyl | ethyl | C | C | hydrogen | bromo |
| 140 | S | benzyl | benzyl | C | C | hydrogen | bromo |
| 141 | S | n-propyl | n-propyl | C | C | hydrogen | bromo |
| 142 | S | ethyl | ethyl | C | C | amino | phenyl |
| 143 | S | benzyl | benzyl | C | C | amino | phenyl |
| 144 | S | n-propyl | n-propyl | C | C | amino | phenyl |
| 145 | S | ethyl | ethyl | C | C | —(CH₂)₂phenyl | hydrogen |
| 146 | S | benzyl | benzyl | C | C | —(CH₂)₂phenyl | hydrogen |
| 147 | S | n-propyl | n-propyl | C | C | —(CH₂)₂phenyl | hydrogen |
| 148 | S | ethyl | ethyl | N | C | — | ethyl |
| 149 | S | ethyl | ethyl | N | C | — | ethyl |
| 150 | S | n-propyl | n-propyl | N | C | — | ethyl |
| 151 | S | 3-chlorobenzyl | 3-chlorobenzyl | C | C | hydrogen | methyl |
| 152 | S | 3-methylbenzyl | 3-methylbenzyl | C | C | hydrogen | methyl |
| 153 | S | 2,4-dimethoxybenzyl | 2,4-dimethoxybenzyl | C | C | hydrogen | methyl |
| 154 | S | 2-methoxybenzyl | 2-methoxybenzyl | C | C | hydrogen | methyl |
| 155 | S | 2-fluorobenyzl | 2-fluorobenzyl | C | C | hydrogen | methyl |
| 156 | S | —CH₂-furyl | —CH₂-furyl | C | C | hydrogen | methyl |
| 157 | S | —CH₂-thienyl | —CH₂-thienyl | C | C | hydrogen | methyl |
| 158 | S | —(CH₂)₃OCH₃ | —(CH₂)₃OCH₃ | C | C | hydrogen | methyl |
| 159 | S | 1,2-dimethoxybenzyl | 1,2-dimethoxybenzyl | C | C | hydrogen | methyl |
| 160 | S | 2-ethylphenyl | 2-ethylphenyl | C | C | hydrogen | methyl |
| 161 | S | 2-ethylphenyl | 2-ethylbenzyl | N | C | — | hydrogen |
| 162 | S | 2-ethylphenyl | 2-ethylphenyl | C | C | methyl | hydrogen |
| 163 | S | 2-ethylphenyl | 2-ethylphenyl | N | C | — | ethyl |
| 164 | S | 2-ethylphenyl | 2-ethylphenyl | C | C | hydrogen | nitro |
| 165 | S | 2,4,6-trimethoxybenzyl | 2,4,6-trimethoxybenzyl | C | C | hydrogen | methyl |
| 166 | S | 3,4,5-trimethoxybenzyl | 3,4,5-trimethoxybenzyl | C | C | hydrogen | methyl |
| 167 | S | 2,4-difluorobenzyl | 2,4-difluorobenzyl | C | C | hydrogen | methyl |
| 168 | S | 2-(2-thienyl)ethyl | 2-(2-thienyl)ethyl | C | C | hydrogen | methyl |
| 169 | S | 2-methoxyethyl | 2-methoxyethyl | C | C | hydrogen | methyl |

In still a further aspect of this embodiment, the ligand inhibitor has structure (IId):

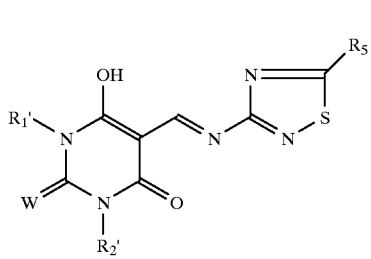

(IId)

wherein n, R₁', R₂', R₅ and W are as defined above. Representative compounds of this embodiment are listed in Table 8.

TABLE 8

Structure (IId)

| Cpd. No. | W | R₁' | R₂' | R₅ |
|---|---|---|---|---|
| 170 | S | ethyl | ethyl | —NHCH₃ |
| 171 | S | n-propyl | n-propyl | —NHCH₃ |

In still a further aspect of this embodiment, the ligand inhibitor has structure (IIe):

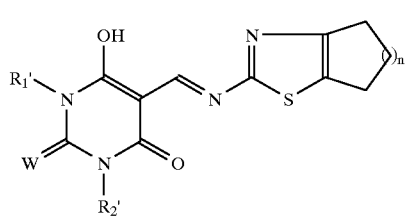

(IIe)

wherein $R_1'$, $R_2'$, W and n are as defined above. Representative compounds of this embodiment are listed in Table 9. Of the compounds listed in Table 9, compound 172 was found to have a Ki<50 nM.

TABLE 9

Structure (IIe)

| Cpd. No. | W | $R_1'$ | $R_2'$ | n |
|---|---|---|---|---|
| 172 | S | n-propyl | n-propyl | 1 |
| 172-1 | S | 2-phenylethyl | ethyl | 1 |

In yet another aspect of this embodiment, the ligand inhibitor has structure (IIf):

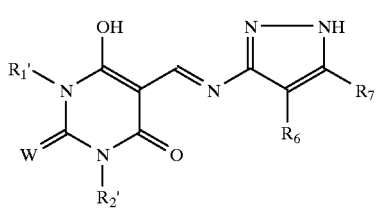

(IIf)

wherein $R_1'$, $R_2'$, $R_6$, $R_7$ and W are as defined above. Representative compounds of this embodiment are listed in Table 10.

TABLE 10

Structure (IIf)

| Cpd. No. | W | $R_1'$ | $R_2'$ | $R_6$ | $R_7$ |
|---|---|---|---|---|---|
| 173 | S | benzyl | benzyl | —CH$_2$CN | —CH$_2$CN |
| 174 | S | n-propyl | n-propyl | —CH$_2$CN | —CH$_2$CN |
| 175 | S | ethyl | ethyl | —CONH$_2$ | hydrogen |
| 176 | S | n-propyl | n-propyl | CONH$_2$ | hydrogen |

In still another aspect of this embodiment, the ligand inhibitor has structure (IIg):

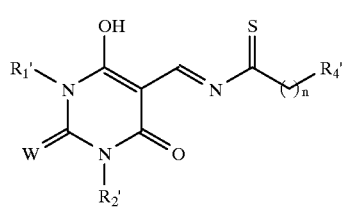

(IIg)

wherein n, $R_1'$, $R_2'$, $R_4'$ and W are as defined above. A preferred compound of this embodiment is listed in Table 11.

TABLE 11

Structure (IIg)

| Cpd. No. | W | $R_1'$ | $R_2'$ | $R_4'$ | n |
|---|---|---|---|---|---|
| 177 | S | ethyl | ethyl | phenyl | 1 |

In yet a further aspect of this embodiment, the ligand inhibitor has structure (IIh):

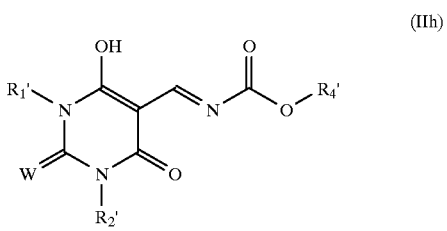

(IIh)

wherein $R_1'$, $R_2'$, $R_4'$ and W are as defined above. A representative compound of this embodiment is listed in Table 12.

TABLE 12

Structure (IIh)

| Cpd. No. | W | $R_1'$ | $R_2'$ | $R_4'$ |
|---|---|---|---|---|
| 178 | S | ethyl | ethyl | phenyl |

In yet a further aspect of this embodiment, the ligand inhibitor has structure (IIi):

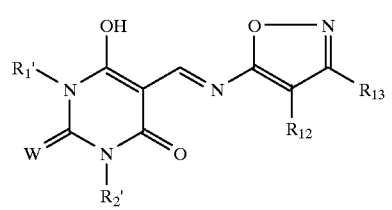

(IIi)

wherein $R_1'$, $R_2'$, $R_{12}$, $R_{13}$ and W are as defined above. Representative compounds of this embodiment are listed in Table 13.

TABLE 13

Structure (IIi)

| Cpd. No | W | $R_1'$ | $R_2'$ | $R_{12}$ | $R_{13}$ |
|---|---|---|---|---|---|
| 179 | S | ethyl | ethyl | hydrogen | methyl |
| 180 | S | n-propyl | n-propyl | hydrogen | methyl |

In yet a further aspect of this embodiment, the ligand inhibitor has structure (IIj):

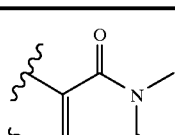
(IIj)

wherein $R_1'$, $R_2'$, W and F are as defined above. A representative compound of this embodiment is listed in Table 14:

TABLE 14

Structure (IIj)

| Cpd. No. | W | $R_1'$ | $R_2'$ | F |
|---|---|---|---|---|
| 181 | S | n-propyl | n-propyl | 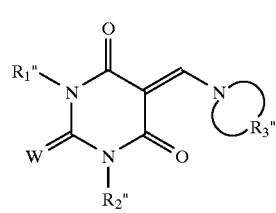 |

In a further embodiment, the ligand inhibitor is a compound having structure (III):

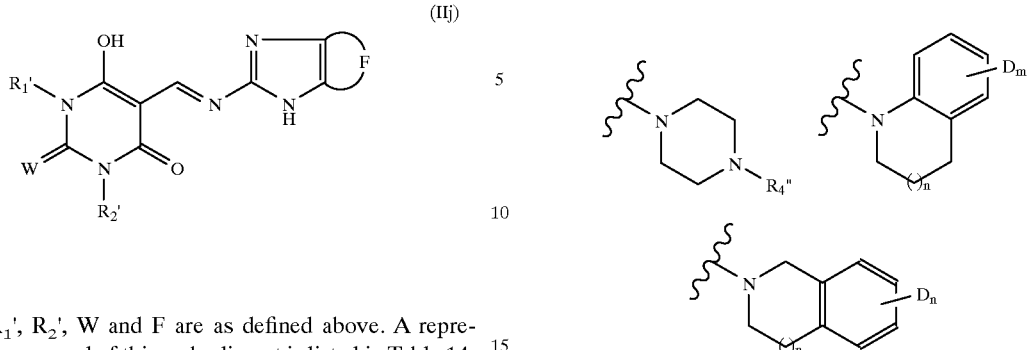
(III)

wherein

W is selected from S and O;

$R_1''$, and $R_2''$ are the same or different and independently selected from $C_{1-8}$alkyl, $C_{2-8}$alkenyl, $C_{2-8}$alkynyl, $C_{1-8}$alkyloxy$C_{1-8}$alkyl, aryl, substituted aryl, aryl$C_{1-8}$alkyl, substituted aryl$C_{1-8}$alkyl, $C_{3-8}$cycloalkyl, $C_{3-8}$cycloalkyl$C_{1-8}$alkyl, $C_{1-12}$heteroaryl, substituted $C_{1-12}$heteroaryl, $C_{1-12}$heteroaryl$C_{1-8}$alkyl, substituted $C_{1-12}$heteroaryl$C_{1-8}$alkyl, $C_{1-12}$heteroaryl$C_{2-8}$alkenyl and substituted $C_{1-12}$heteroaryl$C_{2-8}$alkenyl; and

is selected from the following structures:

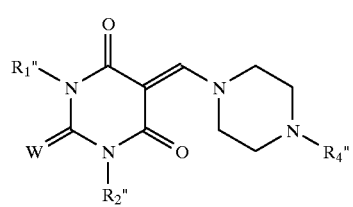

wherein n is 0 or 1;

D is a substituent, m is 0, 1, 2 or 3 and represents the number of D substituents, and each occurrence of D is independently selected from halo, cyano, nitro, acetyl, hydroxy, $C_{1-8}$alkyl, $C_{2-8}$alkenyl, $C_{2-8}$alkynyl, $C_{1-8}$alkyloxy, $C_{3-8}$cycloalkyl, aryl, aryloxy, $C_{1-8}$haloalkyl and $C_{1-8}$cycloalkyl$C_{1-8}$alkyl; and $R_4''$ is selected from aryl and substituted aryl with one or more substituents independently selected from halo and $C_{1-8}$alkyloxy.

In one aspect of this embodiment, the ligand inhibitor has structure (IIIa):

(IIIa)

wherein $R_1''$, $R_2''$, $R_4''$ and W are as defined above. Representative compounds of this embodiment are listed in Table 15.

TABLE 15

Structure (IIIa)

| Cpd. No. | W | $R_1''$ | $R_2''$ | $R_4''$ |
|---|---|---|---|---|
| 182 | S | ethyl | ethyl | 4-fluorophenyl |
| 182-1 | S | 2-phenylethyl | ethyl | 4-fluorophenyl |
| 183 | S | benzyl | benzyl | 4-fluorophenyl |
| 184 | S | n-propyl | propyl | 4-fluorophenyl |

In another aspect of this embodiment, the ligand inhibitor has structure (IIIb):

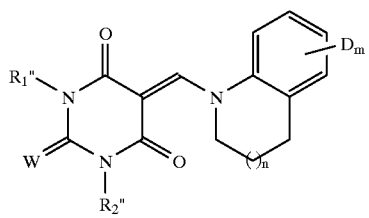

(IIIb)

wherein $R_1''$, $R_2''$, W, $D_m$ and n are as defined above. Representative compounds of this embodiment are listed in Table 16.

TABLE 16

Structure (IIIb)

| Cpd. No. | W | $R_1''$ | $R_2''$ | n | m |
|---|---|---|---|---|---|
| 185 | S | n-propyl | n-propyl | 0 | 0 |
| 186 | S | ethyl | ethyl | 1 | 0 |
| 187 | S | benzyl | benzyl | 1 | 0 |
| 188 | S | n-propyl | n-propyl | 1 | 0 |

In yet a further aspect of this embodiment, the ligand inhibitor has structure (IIIc):

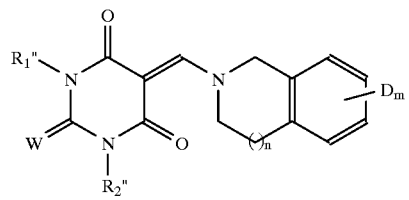

(IIIc)

wherein $R_1''$, $R_2''$, W, $D_m$ and n are as defined above. Representative compounds of this listed in Table 17.

TABLE 17

Structure (IIIc)

| Cpd. No. | W | $R_1''$ | $R_2''$ | n | m |
|---|---|---|---|---|---|
| 189 | S | n-propyl | n-propyl | 0 | 0 |
| 190 | S | ethyl | ethyl | 1 | 0 |
| 190-1 | S | 2-phenylethyl | ethyl | 1 | 0 |
| 191 | S | benzyl | benzyl | 1 | 0 |

Synthesis of Ligand Inhibitors

The ligand inhibitors of structures (I), (II) and (III) above may be synthesized according to the techniques disclosed herein.

Specifically, compounds of structure (I) may be prepared by the following reaction scheme:

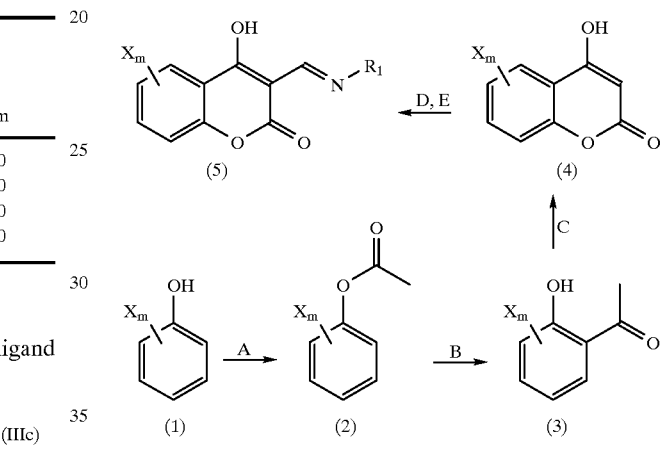

Represents reactions for the synthesis of compounds having structure (I) (i.e., compound (5)) are illustrated in Example 1 methods A through E above. In brief, a phenol acetate (2) is prepared from the corresponding phenol or substituted phenol (1) by method A. In method B, the corresponding 2'-hydroxyacetophenone (3) is made, followed by the synthesis of a corresponding 4-hydroxycoumarin (4) via method C. Compounds of structure (I) are then prepared from compound (4) by method D or E.

Compounds of structure (II) and (III) may be prepared by the following reaction scheme:

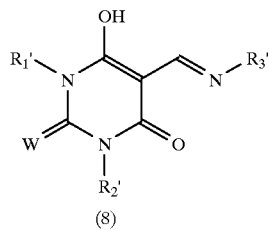

(8)

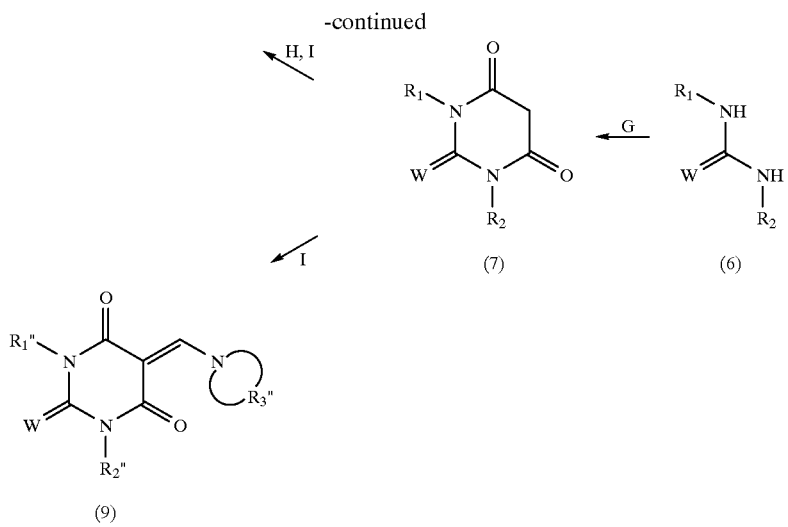

Representative reactions for the synthesis of compounds having structure (II) and (III) are illustrated in Example 2 for methods G, H and I above. In short, by method G an appropriately N,N'-substituted thiourea (6) is converted to the corresponding N,N'-substituted barbituric acid (when W is oxygen) or 2-thiobarbituric acid (when W is sulfur) compound (7). By methods H or I the compound of structure (II) (i.e., compound (8)) is synthesized from compound (7), and by method I the compound of structure (III) (i e., compound (9)) is prepared from compound (7).

Evaluating Activity of Ligand Inhibitors

A ligand inhibitor of this invention may be evaluated for its ability to displace CRF from the CRF/CRF-BP complex and secondly, by evaluating its ability to bind the CRF receptor.

Candidate ligand inhibitors may be screened for their ability to displace CRF from the CRF/CRF-BP complex by biological assay or by in vitro assay. One suitable biological assay is the measurement of ACTH release from cultured pituitary cells. This assay is performed in the following manner. Anterior pituitary glands from rats are washed six times with sterile HEPES buffer and transferred to a solution containing collagenase. After subsequent transfer to a 25 ml Bellco dispersion flask, the pituitaries are stirred for 30 minutes at 37° C., triturated, incubated for a further 30 minutes, and again triturated. The partially dispersed cells are then collected by centrifugation. The cell pellet is resuspended in 10 ml of neuraminidase and again collected by centrifugation. The pellet is reconstituted in 25 ml of BBM-P (BBM (Irvine Scientific) plus 100 $\mu$g/L, cortisol, 1 $\mu$g/L insulin, 0.1 $\mu$g/L EGF$_2$, 0.4 $\mu$g/L T$_3$, 0.7 $\mu$g/L PTH, 10 $\mu$g/L glucagon, and 2% fetal bovine serum), centrifuged again, and the resultant pellet is finally reconstituted in BBM-P. The cells are then plated at a density of 50,000–100,000/well in a 48 well plate and incubated for 2 days. On the day of assay the cells are washed once with BBM-T in preparation for stimulation with the peptide candidates or CRF. Cells are stimulated with a maximally stimulating dose of h/rCRF (1 nM) and ACTH release is measured by RIA or immunoradiometric assay. When a blocking concentration of CRF-BP is added, the amount of ACTH that is released is reduced and expressed as a fraction of the maximal release. The ligand inhibitor is added at various doses. The potency of the peptide in displacing CRF from CRF-BP is measured by the amount of ACTH release expressed as a fraction of the maximal release caused by CRF given alone.

A preferred mode of screening candidate ligand inhibitors is by an in vitro ligand immunoradiometric assay (LIRMA). For LIRMA, CRF-BP may be isolated from brain tissue, serum or cells expressing a recombinant form. Recombinant hCRF-BP may be produced in Chinese Hamster Ovary (CHO) cells bearing the pSG5-hA3 and RSV-neo plasmids. Stable CHO transfectants are cloned by dilution under G418 (Sigma Chemical, St. Louis, Mo.) selection and maintained in Dulbecco's Modified Eagle Medium supplemented with 2 mM L-glutamine and 3% fetal bovine serum. In order to scale up production of hCRF-BP, transfected CHO cells are inoculated into a 10,000 MWCO bioreactor (Cell Pharm Micro Mouse, Unisyn Technologies, Tustin, Calif.). Enriched medium is harvested from the bioreactor daily and stored at −20° C. until purification. Closed roller bottles containing recombinant cells and tissue culture medium, which are slowly rotated in a 37° C. environment, may alternatively be used.

hCRF-BP may be purified by a 3-step process, with fractions from each step being evaluated using the assay described below. First, enriched medium is affinity-purified using a Bio Pilot chromatography device (Pharmacia LKB Biotechnology, Uppsala, Sweden). Human CRF is coupled to Affi-Prep 10 (Bio Rad Laboratories, Richmond, Calif.) via primary amino groups using N-hydroxysuccinimide. After coupling, the affinity gel is packed into an XK16 or equivalent column (Pharmacia LKB Biotechnology, Uppsala, Sweden). Affinity purification consists of percolating enriched medium through the column at 2 ml/minutes, washing with 10 bed volumes of 100 mM HEPES HCl (pH 7.5) at 5 ml/minutes and eluting 1 bed volume fractions using 80 mM triethylammonium formate (pH 3.0) containing 20% acetonitrile at 5 ml/minutes. Elution under mildly basic conditions, e.g., pH about 10.5, may alternatively be used.

Secondary purification utilizes gel chromatography. Affinity-pure hCRF-BP is lyophilized and reconstituted in 6M guanidine-HCl buffered with 0.1M ammonium acetate (pH 4.75). An FPLC device is used in conjunction with two Superose 12 HR 10/30 columns (Pharmacia LKB Biotechnology, Uppsala, Sweden) connected in series for this purification step. The affinity-pure hCRF-BP is loaded in 1 ml and subsequently eluted with 6M guanidine HCl/0.1M ammonium acetate (pH 4.75) at 0.4 ml/minutes, collecting fractions every minute.

Active fractions from the secondary purification are then subjected to reversed-phase HPLC. The HPLC device consists of 2 model 100A pumps (Beckman, Palo Alto, Calif.), an Axxiom HPLC controller (Cole Scientific, Calabasas, Calif.), a Spectroflow 773 absorbance detector set to 214 nm (Kratos Analytical, Ramsey, N.J.), and a Pharmacia. model 482 chart recorder (Pharmacia LKB Biotechnology, Uppsala, Sweden). Buffer A is 0.1% trifluoroacetic acid (TFA)/5% acetonitrile, and buffer B is 0.1% TFA/80% acetonitrile. Sequential 1 ml injections of affinity-pure, sized hCRF-BP are applied to a semipreparative C4 HPLC column (Vydac, Hesperia, Calif.) under isocratic conditions with a flow rate of 2.5 ml/minute in 25% B buffer. After the passage of the final salt peak, a single gradient elution is performed starting at 25% B buffer and increasing to 95% B buffer over 30 minutes. The predominant absorbance peak is then quantitated by hCRF-BP IRMA and by amino acid analysis.

In LIRMA CRF-BP isolated from brain tissue, serum, or cells expressing a recombinant form, is added to wells of a 96-well plate, to small polypropylene microfuge tubes, or to glass borosilicate tubes in a binding buffer (0.02% NP-40 in 50 mM phosphate-buffered saline). $^{125}$I-h/rCRF (New England Nuclear) and the candidate ligand inhibitor at 10 $\mu$M are added and the reaction is incubated for 1 hour at room temperature. An appropriately diluted anti-CRF-BP antibody, such as a rabbit anti-hCRF-BP (Potter et al., *Proc. Natl. Acad. Sci. USA* 89:4192–4196, 1992) is added to each tube, and after further incubation, bound complexes are precipitated by the further addition of a goat anti-rabbit antibody. The precipitate containing $^{125}$I-CRF is collected by centrifugation and the amount of radioactivity in the pellet is determined by a gamma counter. If the candidate ligand inhibitor displaces CRF from CRF-BP, the pellets will contain less radioactivity in comparison to controls in which no candidate peptide is added. Maximum inhibition (i.e., 100%) of the binding of $^{125}$I-h/rCRF to the CRF-BP is defined by the amount of radioactivity left in the pellets after incubation with 10 $\mu$M of the CRF-BP peptide ligand h/rCRF (6-33). Thus, the binding potency of the candidate ligand inhibitor will be measured relative to the potency of the standard h/rCRF (6-33). Preferably, there is at least 50% inhibition when ligand inhibitor is present.

The inhibitory binding affinity constant ($K_i$) is important; it is viewed in proper perspective as per its value relative to the $K_i$ for human CRF which, from this assay, is found to be 0.17±0.01 nanomolar (nM). Thus, a ligand having a $K_i$ of less than that of hCRF will bind more strongly to hCRF-BP than will hCRF itself, and a ligand having a higher value will have a relatively lower binding affinity. Therefore, because the desire is to compete reasonably effectively with hCRF for binding with hCRF-BP, the lower $K_i$ value the agent or peptide has, the more valuable it will be for this purpose. Preferably, the agent will have a $K_i$ value of about 100 nM or less, more preferably a $K_i$ value of about 50 nM or less, and most preferably, a $K_i$ value of less than about 20 nM.

A high through-put screening using the LIRMA assay as described, or other methods including ACTH release and 2-site ELISA, may be used to identify ligand inhibitors that displace CRF from the CRF/CRF-BP complex. In a first round of screening, all potential candidates are assayed at a single dose of 10 $\mu$M. Any compound which gives greater than 50% inhibition at 10 $\mu$M is then selected for further screening. The activity of all candidates meeting this criteria is confirmed by a second round of screening using a 6 point-dose response curve. IC-50 values are calculated and those candidates with a value in the range of 10–100 $\mu$M are further examined to ensure that the candidate compound is displacing CRF from the CRF/CRF-BP complex and not interfering with antibody binding to the CRF-BP. Specific displacement of CRF is verified in an assay performed as described for LIRMA, except that 0.2 nM $^{125}$I-hCRF-BP is added in place of unlabeled CRF-BP.

Ligand inhibitors may also be screened by an in vitro assay in which bound and free CRF are separated by detergent phase separation. Briefly, within one embodiment, CRF-BP isolated as described above is incubated with $^{125}$I-h/rCRF and the candidate ligand inhibitor at 10 $\mu$M in a binding buffer (0.02% NP-40 in 50 mM phosphate-buffered saline). Following incubation of 1–2 hours at room temperature, a detergent, such as octylphenoxypolyethoxyethanol, sold as Triton X-114™, is added and mixed by vortexing. Triton X-114™ and other nonionic detergents are insoluble in water above their cloud point temperature. At this temperature, there occurs a microscopic phase separation. Below this temperature, the detergents form clear micellar solutions and above this temperature, two clear phases, one depleted and one enriched in detergent, are formed. The cloud point temperature of Triton X-114™ is 20° C. As such, Triton X-114™ is preferred. CRF, which has amphiphilic alpha helices, is more soluble in Triton X-114™ and thus partitions to the detergent phase. In contrast, CRF bound to CRF-BP is more soluble in an aqueous solution. Thus, a phase separation of Triton X-114™ and the aqueous solution will segregate bound and free CRF. Phase separation is conveniently accomplished by centrifugation. The aqueous phase (on top) may be removed and the amount of $^{125}$I-h/rCRF determined. A reduction of radioactivity relative to that obtained in the absence of ligand inhibitor means that the ligand inhibitor displaced CRF from CRF-BP. Maximum inhibition (i.e., 100%) of the binding of $^{125}$I-h/rCRF to the CRF-BP is defined by the amount of radioactivity in the aqueous phase after incubation with 10 $\mu$M of the CRF-BP peptide ligand h/rCRF (6-33). Thus, the binding potency of the candidate ligand inhibitor will be measured relative to the potency of the standard h/rCRF (6-33). Preferably, there is at least 50% inhibition when ligand inhibitor is present.

In addition, this assay has broad application in screening for neuropeptide binding proteins in general. Some neuropeptides, such as NPY, have similar physical characteristics to CRF in that they are both very hydrophobic and have alpha helices. As such, NPY should be more soluble in a nonionic detergent, such as Triton X-114™, than in aqueous solutions. Given that NPY or other neuropeptides of interest will generally partition into the Triton X-114™ detergent phase, the method described above may be generally employed to screen for neuropeptide-binding proteins. Briefly, by way of example, tissue from various organs is homogenized in 1% NP-40/PBS solubilization buffer. Particulate matter is removed by centrifugation for 10 minutes at 3000×g. A 50 $\mu$l aliquot from the supernatant is incubated with 500 pM of the $^{125}$I-labeled neuropeptide and the assay is performed as above. Serum or plasma may also be used as a potential source of neuropeptide-binding proteins. A range of concentrations (0.1–1000 nM) of unlabeled neuropeptide is coincubated with the radiolabeled neuropeptide to assess whether the putative binding protein specifically binds the radiolabeled neuropeptide. When binding is specific, the radioactivity remaining in the aqueous phase after Triton X-114™ separation is decreased. Using this method, an IC-50 value can be established for each neuropeptide and tissue extract.

Furthermore, this method may be employed to screen for ligand inhibitors of the neuropeptide to its neuropeptide-binding protein. Briefly, radiolabeled neuropeptide is incubated with the neuropeptide-binding protein or soluble receptor and the reaction performed as described above. For these assays, either recombinant neuropeptide-binding protein or receptor or crude neuropeptide-binding protein isolated from tissue sample may be used.

A preferred ligand inhibitor either has a low affinity antagonist effect at the CRF receptor or has a 100-fold selectivity to the CRF binding protein. Therefore, compounds with an IC-50 value in the range of 10–100 $\mu$M and a specific inhibition of the CRF/CRF-BP complex are further tested for binding to the CRF receptors. The ability of the ligand inhibitor to antagonize the CRF receptor is assessed in a cAMP production assay. The assay compares the potency of the ligand inhibitor to increase levels of free CRF which thereby bind the CRF receptor, and stimulate cAMP production. The test cell lines express the CRF receptor as stable transfectants. The assay is performed according to Battaglia et al. (*Synapse* 1:572, 1987) with minor modifications. Test cells are incubated for 1 hour with various concentrations of CRF and ligand inhibitors. The cells are washed, and intracellular cAMP is released upon incubation of the cells for 16–18 hours and is subsequently extracted in 20 mM HCl, 95% ethanol. The lysate is lyophilized and subsequently solubilized in a sodium acetate buffer. The levels of cAMP are measured using a single antibody kit, such as the one from Biomedical Technologies (Stoughton, Mass.).

As an alternative to carrying out the foregoing competitive in vitro evaluation assays, the ligand inhibitor can be evaluated in a binding assay with the human CRF receptor. The human CRF receptor and a binding assay for such receptor and human CRF are described in Chen et al., *Proc. Natl. Acad. Sci. USA* 90:8967–8971, 1993, the disclosure of which is incorporated herein by reference. The agent may be evaluated with radioactively labeled [$Nle^{21}$, $Tyr^{32}$] oCRF to compute an inhibitory binding affinity constant ($K_i$). Preferably the agent has a receptor $K_i$ of at least about 100 nM and more preferably greater than 1000 nM. It may alternatively be satisfactory to use the rat CRF receptor because human CRF and rat CRF have the identical amino acid sequence.

An additional assay using rat anterior pituitary cells to measure ACTH secretion can be carried out to determine whether a ligand inhibitor functions as a CRF agonist of hCRF receptors. The procedure which is used is that as generally set forth above except that only ligand inhibitor is added to the cells. Antagonistic action may be determined by performing the assay in the presence of a challenge dose of CRF. The performance of the ligand inhibitor is compared to the performance of what has become a standard antagonist for this purpose, such as CD-$Phe^{12}$, $Nle^{21, 38}$]-rCRF(12-41) or a fragment of alphahelical CRF(AHC), such as AHC (9-41).

The above-identified in vitro assays to measure CRF agonist and antagonist activity from the standpoint of stimulation of ACTH secretion may be performed using hCRF (6-33) and hCRF (9-33). As a result of such assays, hCRF (6-33) is shown to have a CRF agonist bioactivity much less than the standard oCRF, which is arbitrarily considered as 1.0. This peptide does not exhibit substantial CRF antagonist activity. Because this peptide has less than about 0.1% of the CRF agonist activity of the standard peptide, it is acceptable from this standpoint. The peptide hCRF (9-33) is even a weaker CRF agonist, having substantially less than 0.01% of the activity of oCRF. The desire is that the ligand inhibitor which is employed will not bind strongly to CRF receptors.

It is generally believed that a ligand inhibitor should have less than about 25% of the CRF agonist activity of oCRF and that it should not exhibit substantial CRF competitive antagonist activity. Preferably, it should have less than 5% of the antagonist activity of the present standard peptide [$DPhe^{12}$, $Nle^{21,38}$]-hCRF(12-41). However, it should be understood that the lower its value in such an assay, the better it should function in this method because its potential blocking effect as a result of binding to CRF receptors will be minimized.

Increasing the level of CRF

The present invention provides methods for increasing the level of free CRF in the brain through the administration of a ligand inhibitor of a CRF/CRF-BP complex. The increase in level of free CRF may be measured by in vitro assays, such as ELISA, stimulation of ACTH release, or stimulation of cAMP production. In any of these assays, an increase in free CRF due to administration of the ligand inhibitor is measured relative to a reference ligand inhibitor, in this case h/rCRF (6-33). A minimal acceptable value of increase is 10% of the value for h/rCRF (6-33); a moderate value is 50%, a preferred value is 80%, and a particularly preferred value is 100%.

Within the methods described herein, the level of free CRF may be measured by two-site ELISA on homogenates of brain samples, cerebrospinal fluid, or on other bodily tissues and fluids. Total CRF is first quantitated as follows. Wells of an ELISA plate are coated with an anti-CRF antibody, such as protein G purified-sheep anti-CRF. The plates are washed, and unbound sites on the plate are blocked with an irrelevant protein, such as casein, bovine serum albumin, or the like. Prepared tissue samples and standards containing known amounts of CRF are added to wells and allowed to bind at room temperature. Following binding, plates are again washed, and a different anti-CRF antibody, such as RC-70, a rabbit anti-human CRF antibody, is added. RC-70 is not only from a different species, but also detects different epitopes than the sheep anti-CRF used to coat the plates. After washing, an enzyme-conjugated antibody that detects RC-70, or the equivalent, is added. Alternatively, RC-70 antibody may be enzyme-conjugated. Preferred conjugates are horseradish peroxidase and alkaline phosphatase, but one skilled in the art will recognize that many different acceptable alternatives are available, including a radiolabel instead of an enzyme. Enzyme substrate is added, and color development proceeds. After termination of the reaction, absorbance measurements are used to quantify the amount of total CRF present in the tissue sample. One skilled in the art will recognize that monoclonal antibodies or antibody fragments may be used in place of the polyclonal antibodies in this assay.

In a similar manner, bound CRF may be quantitated by ELISA by coating plates with an anti-CRF-BP antibody followed by detection of the bound CRF with an anti-CRF antibody. Bound CRF can be specifically displaced by the CRF-BP ligand $\alpha$-helical oCRF(9-41) resulting in a decrease in the signal detected. Alpha helical oCRF(9-41) is used for the displacement as it does not crossreact with RC-70, anti-CRF antibody. Furthermore, the displaced CRF present in the supernatants may then be assayed by two-site ELISA, as described. Free CRF may then be determined by calculation of the difference between total CRF and bound CRF or by a direct assay. In a direct assay, following capture of the bound complex by the anti-CRF-BP monoclonal antibody, the supernatants are removed and the free CRF measured in a two-site ELISA, as described.

In addition to the described in vitro assays that measure the amount of total, bound, and free CRF in tissues or in cerebrospinal fluid, other procedures may be performed in vivo. These include MRI, PETSCAN, spectscanning or other similar imaging techniques, some of which use a radiolabeled ligand to CRF-BP or to CRFreceptors. A preferred method is image analysis using PET position-emitting ligands (e.g., $^{11}$c, $^{18}$F) of single photon-emitting ligands (e.g., $^{123}$I-labeled ligand to CRF-BP or to CRF receptors). Free CRF levels are correlated to the amount of binding of the radiolabeled ligand. An increase in free CRF levels is manifested by a decreased binding of the radiolabeled ligand to the CRF-BP and CRF receptors. Within this imaging technique, an increase in free CRF levels of about 10%–30% or more would be sufficient in the context of the present invention.

Within the context of the present invention, administration of effective amounts of ligand inhibitor of the CRF/CRF-BP complex may be used to treat diseases or syndromes in which there are decreased levels of CRF. CRF levels may be measured directly in cerebrospinal fluid or in the brain by imaging or other methods (e.g., cAMP production, ACTH release, or two-site ELISA). Such diseases or syndromes include symptoms of dementia or learning and memory loss, obesity, chronic fatigue syndrome, atypical depression, post-partum depression, seasonal depression, hypothyroidism, post-traumatic stress syndrome, nicotine withdrawal, vulnerability to inflammatory disease. Definitions of these syndromes (except for obesity, chronic fatigue syndrome, and vulnerability to inflammatory diseases) are provided in *Diagnosis and Statistical Manual of Mental Disorders* (4th ed.), American Psychiatric Association, Washington, D.C., 1994; (hereinafter DSM-IV).

CRF-Related Peptides

Other peptide molecules, which are distinct from CRF, bind CRF-BP. For example, the human neuropeptide urocortin (Vaughan et al., *Nature* 378:287, 1995) has a high affinity for human CRF-BP. Some non-mammalian peptides such as sauvagine and urotensin, also bind CRF-BP with high affinity. Thus, CRF-BP may be a modulator of a family of CRF-related peptides. For example, in vitro experiments show that rat urocortin can disrupt the CRF/CRF-BP complexes normally found in human brain tissue. Such disruption has the effect of increasing free CRF levels, thus making more CRF available for binding to its receptors. The ligand inhibitors of the present invention may also be used to elevate free levels of urocortin and other members of the CRF family in mammals. Assays for measuring the increase of urocortin (as well as other CRF-related peptides) are performed essentially as described herein for CRF, except that the appropriate detection molecules are employed (e.g., antibody to urocortin). Moreover, urocortin, sauvagine, urotensin, and the like and their analogues may be used to inhibit CRF/CRF-BP complexes and raise free CRF levels or inhibit urocortin/CRF-BP complexes and raise free urocortin levels. Given the effects of urocortin on lowering blood pressure, such ligand inhibitors may be useful in treating hypertension. In addition, urocortin appears to significantly suppress feeding behavior in animals, and therefore, such ligand inhibitors may be useful in modulating food intake.

Improving Learning and Memory

As noted above, the present invention provides methods for improving learning and memory through the administration to a patient of a therapeutically effective amount of a ligand inhibitor of a CRF/CRF-BP complex. Such patients may be identified through a clinical diagnosis based on symptoms of dementia or learning and memory loss. Individuals with an amnesic disorder are impaired in their ability to learn new information or are unable to recall previously learned information or past events. The memory deficit is most apparent on tasks to require spontaneous recall and may also be evident when the examiner provides stimuli for the person to recall at a later time. The memory disturbance must be sufficiently severe to cause marked impairment in social or occupational functioning and must represent a significant decline from a previous level of functioning. The memory deficit may be age-related or the result of disease or other cause.

Dementia is characterized by multiple clinically significant deficits in cognition that represent a significant change from a previous level of functioning. Memory impairment involving inability to learn new material or forgetting of previously learned material is required to make the diagnosis of a dementia. Memory can be formally tested by asking the person to register, retain, recall and recognize information. The diagnosis of dementia also requires at least one of the following cognitive disturbances: aphasia, apraxia, agnosia or a disturbance in executive functioning. These deficits in language, motor performance, object recognition and abstract thinking, respectively, must be sufficiently severe in conjunction with the memory deficit to cause impairment in occupational or social functioning and must represent a decline from a previously higher level of functioning.

In addition, a number of biochemical tests that correlate levels of CRF with impaired learning and memory may be utilized. For instance, the level of free CRF in the cerebrospinal fluid may be measured by ELISA or RIA. Additionally, or in place of the assays, brain imaging as described with a labeled ligand specific to the CRF-BP or CRF receptor may be used to quantitate free receptor or CRF-BP, thus allowing one to know that free CRF is decreased. Finally, imaging of the brain with a ligand specific to unbound CRF may be used to directly assay the amount of free CRF in the brain.

The patient's minimental status is recorded by the Minimental Test for Learning and Memory, a standard test used by clinicians to determine if a patient has impaired learning and memory (Folstein et al., *J. Psychiatric Res.* 12:185, 1975). This test involves a number of simple tasks and written questions. For instance, "paired-associate" learning ability is impaired in amnesiac patients of several types including those suffering from head trauma, Korsakoff's disease or stroke (Squire, 1987). Ten pairs of unrelated words (e.g., army-table) are read to the subject. Subjects are then asked to recall the second word when given the first word of each pair. The measure of memory impairment is a reduced number of paired-associate words recalled relative to a matched control group. This serves as an index of short-term, working memory of the kind that deteriorates rapidly in the early stages of dementing or amnesiac disorders.

Improvement in learning and memory constitutes either (a) a statistically significant difference between the performance of ligand-inhibitor treated patients as compared to members of a placebo group; or (b) a statistically significant change in performance in the direction of normality on measures pertinent to the disease model. This strategy has been successfully employed in identifying therapeutically useful cholinomimetics for memory improvement. Animal models or clinical instances of disease exhibit symptoms which are by definition distinguishable from normal controls. Thus, the measure of effective pharmacotherapy will be a significant, but not necessarily complete, reversal of symptoms. Improvement can be facilitated in both animal and human models of memory pathology by clinically effective "cognitive enhancing" drugs which serve to improve performance of a memory task. For example, cognitive enhancers which function as cholinomimetic replacement therapies in patients suffering from dementia and memory loss of the Alzheimer's type significantly improve short-term working memory in such paradigms as the paired-associate task (Davidson and Stem, 1991). Another potential application for therapeutic interventions against memory impairment is suggested by age-related deficits in performance which are effectively modeled by the longitudinal study of recent memory in aging mice (Forster and Lal, 1992).

In animals, several established models of learning and memory are available to examine the beneficial cognitive enhancing effects and potential anxiety-related side effects of activation of CRF-sensitive neurons. The cognitive enhancing effects are measured by the Morris maze (Stewart and Morris, in *Behavioral Neuroscience,* R. Saghal, Ed. (IRL Press, 1993) p. 107) the Y-maze (Brits et al., *Brain Res. Bull.* 6, 71 (1981)), one-way active avoidance test, and two-way passive avoidance test; anxiety-related effects are evaluated in the elevated plus-maze. (Pellow et al., *J. Neurosci. Meth.* 14:149,1985.)

The Morris water maze is one of the best validated models of learning and memory, and it is sensitive to the cognitive enhancing effects of a variety of pharmacological agents (McNamara and Skelton, *Brain Res. Rev.* 18:33, 1993). The task performed in the maze is particularly sensitive to manipulations of the hippocampus in the brain, an area of the brain important for spatial learning in animals and memory consolidation in humans. Moreover, improvement in Morris water maze performance is predictive of clinical efficacy of a compound as a cognitive enhancer. For example, treatment with cholinesterase inhibitors or selective muscarinic cholinergic agonists reverse learning deficits in the Morris maze animal model of learning and memory, as well as in clinical populations with dementia (McNamara and Skelton, 1993; Davidson and Stem, 1991; McEntee and Crook, 1992; Dawson et al., 1992). In addition, this animal paradigm accurately models the increasing degree of impairment with advancing age (Levy et al., 1994) and the increased vulnerability of the memory trace to pre-test delay or interference (Stewart and Morris, 1993) which is characteristic of amnesiac patients.

The test is a simple spatial learning task in which the animal is placed in tepid water, which is opaque due to the addition of powdered milk. The animals learn the location of the platform relative to visual cues located within the maze and the testing room; this learning is referred to as place learning.

As discussed in more detail below (see Example 6), 15 minutes prior to training on each of days 1–3, groups of animals orally receive control solution or a dosage of the ligand inhibitor. Control animals typically reach the platform within five to ten seconds after three days of training. The measure of the memory modulator effects of a ligand inhibitor is a shift of this time period. Administration of a ligand inhibitor results in a dose-dependent increase in availability of synaptic CRF and a behavioral dose-dependent increase in acquisition and memory retention.

The Y-maze test based on visual discrimination is another assay of learning and memory in animals. In this maze, two arms of the maze end in a translucent plastic panel behind which there is a 40-watt electric bulb. The start box is separated from the third arm by a manually-activated guillotine door. In the first trial, all animals are allowed to explore the maze for 5 minutes, and food pellets are available in each arm. On the second day, each animal is placed in the start box with the door closed. When the door is opened, the animal is allowed to move down the arms and eat the pellets which are located in both arms. On the third day, animals receive six trials in groups of three where one arm is closed at the choice point, no discriminative stimulus is present, and two food pellets are available in the open goal box. On days 4–10, a light at the end of the arm with the food pellets is illuminated and ten trials are run, again in groups of three. The time it takes for the animal to reach the food pellets is recorded.

The effectiveness of a ligand inhibitor to improve learning and memory in the Y-maze is tested as follows. Fifteen minutes prior to each of the blocks of training trials on days 4–10, groups of animals orally receive control solutions or doses of a ligand inhibitor. Control animals are expected to make 50% correct choices. The measure of efficacy of treatment on memory is an increase in correct responses.

The one-way active avoidance test is another assay of learning and memory in animals. It may be used to assess improvement in age-related memory deficits. An animal is placed in a footshock compartment; an opening door to a safe compartment serves as a signal for avoidance. Briefly, in this test an animal is placed in a Skinner box enclosure that contains a grid floor composed of stainless steel bars. A seven watt light and tone generator at each end of the box serve as conditioned stimuli. A rat or mouse is initially trained by being placed in the footshock compartment facing away from the door. A shock is administered simultaneously with the door opening to the safe compartment. At intervals, the test is repeated, only the shock is delayed for 10 seconds after the door is opened. The time it takes the animal to leave the footshock compartment is recorded.

The effectiveness of a ligand inhibitor to improve memory and learning in the one-way avoidance or control solution is tested as follows. Animals are given the ligand inhibitor 15 minutes prior to training. Twenty-four hrs later, the groups are tested for retention, without further administration of ligand inhibitor. The measure of efficacy is a shortened latency time to leaving the footshock compartment.

The two-way passive avoidance test is another assay of learning and memory. An animal is placed in the safe compartment of the Skinner box and when it enters the footshock compartment, the door is closed and a mild shock is administered. The latency time for entering the second compartment is recorded. Memory is tested 1 to 7 days later. At this time, a shock is not administered.

The effectiveness of a ligand inhibitor to improve learning and memory is tested as follows. Immediately prior to training, groups of animals orally receive control solutions or doses of ligand inhibitor. Latency time for entering the footshock compartment is then determined.

The elevated plus maze test measures anxiogenic responses in an approach-avoidance situation involving an exposed, lighted space versus a dark, enclosed space. Both spaces are elevated and are set up as two runways intersecting in the form of a plus sign. This type of approach-avoidance situation is a classical test of "emotionality" and is very sensitive to treatments that produce disinhibition and stress. Animals are placed in the center of the maze and are allowed free access to all four arms in a five minute testing period. The time spent in each arm is recorded.

In humans, methods for improving learning and memory may be measured by such tests as the Wechsler Memory Scale or a pair-associate memory task. The Wechsler Memory Scale is a widely-used pencil-and-paper test of cognitive function and memory capacity. In the normal population, the standardized test yields a mean of 100 and a standard deviation of 15, so that a mild amnesia can be detected with a 10–15 point reduction in the score, a more severe amnesia with a 20–30 point reduction, and so forth (Squire, 1987). During the clinical interview, a battery of tests, including, but not limited to, the Minimental test, the Wechsler memory scale, or paired-associate learning are applied to diagnose symptomatic memory loss. These tests provide general sensitivity to both general cognitive impairment and specific loss of learning/memory capacity (Squire, 1987). Apart from the specific diagnosis of dementia or amnestic disorders, these clinical instruments also identify age-related cognitive decline which reflects an objective diminution in mental function consequent to the aging process that is within normal limits given the person's age (DSM IV, 1994). As noted above, "improvement" in learning and memory is present within the context of the present invention if there is a statistically significant difference in the direction of normality in the paired-associate test, for example, between the performance of ligand-inhibitor treated patients as compared to members of the placebo group or between subsequent tests given to the same patient.

Decreasing Food Intake

As noted above, the present invention provides methods for decreasing food intake through the administration to a patient of a therapeutically effective amount of a ligand inhibitor of a CRF/CRF-BP complex. CRF has been shown to be an important modulator of food intake. For example, administration of CRF agonists or conditions that elevate endogenous CRF levels (e.g., stress) diminish food intake (Appel et al., *Endoc.* 128:3237, 1991; Krahn and Gosnell, *Psychiat. Med.* 7:235, 1989; McCarthy et al., *Am. J. Physiol.* 264:E638, 1993). Thus, administration of CRF causes significant decrease on nocturnal food intake (Gosnell et al., *Peptides* 4:807, 1983), lowered body weight in rats (Hotta et al., *Life Sci.* 48:1483, 1991) and increased temperature response in brown adipose tissue (LeFeuvre et al., *Neuropharmacol.* 26:1217, 1987). Furthermore, neuropeptide Y (NPY), which is the strongest known stimulus of food intake, can be potentiated in its effect upon co-administration of an antagonist of the CRF receptor.

Patients may be identified by being obese. An obese individual weighs more than a target weight considered normal for that person's age, gender and height and can be identified objectively by a body mass index (BMI— calculated as weight in kilograms/height in meters$^2$) at or higher than the 85th percentile of the same reference population (National Center for Health Statistics, "Obese and Overweight Adults in the United States." Series 11, No. B0, U.S. Government Printing Office, Washington, D.C., 1983). In addition, evidence that CRF is involved for a particular individual may be obtained by demonstrating decreased CRF levels in the cerebrospinal fluid or by brain imaging as described above. Because the hypothalamus is a common brain area mediating the effects of CRF on food intake and endocrine parameters, alterations in pituitary hormone concentration may also reflect altered levels in hypothalamic CRF.

A decrease in food intake may be measured both in the delayed initiation of a meal and the reduction in the overall duration or quantity of food consumption. Smith, "Satiety and the Problem of Motivation," in D. W. Pfaff (ed.), *The Physiological Mechanisms of Motivation,* Springer-Verlag, New York, pp. 133–143, 1982. In addition, the selection of particular nutrients in a food choice situation serves as a supplemental measure of specific hunger (Rozin, *Adv. Study Behav.* 6:21, 1976).

There are two established animal models of appetite regulation. One is a simple measurement of food intake, and the second is a measurement of diet self-selection in a cafeteria environment. In the first method, food intake is limited for 24 hours followed by two hours of access to a preweighed portion of laboratory chow in the animal's home cage. Food intake is measured at 60 and 120 minutes by weighing the remaining pellets. These tests may also be performed on animals that are obese due to genetic mutations and which effectively reproduce symptoms of overeating and deranged nutrient selection (Argilés, *Prog. Lipid Res.* 28:53, 1989; Wilding et al., *Endocrinol.* 132:1939, 1993).

In the cafeteria environment, diets are specially formulated with differing proportions of macronutrients, such as carbohydrate, protein, and fat, so as to measure preference for specific nutrients based on sensory attractiveness or post-ingestive benefit. Diet selection is altered, in part, by a wide variety of neurochemical systems. These tests are useful for detection of subtle changes in food intake regulation which impact phenomena, such as craving or binging, and are relevant for the diagnosis of eating disorders, such as anorexia nervosa and obesity. Following establishment of a baseline for animals, 15 minutes prior to testing each animal receives an oral dose of a ligand inhibitor. Food intake is measured as described for the feeding test or the diet self-selection in the cafeteria environment, and test results are compared to baseline.

In addition, overeating in an animal model of nicotine withdrawal and in genetically obese rats (Zucker strain) provide other models to test the effect of a ligand inhibitor on appetite regulation. Briefly, in the nicotine withdrawal model, animals are administered nicotine in a chronic fashion. These animals show inhibition of normal weight gain and reduction of food and water intake. Upon cessation of nicotine treatment, animals significantly increase both body weight and intake of food and water. The effect of ligand inhibitors on appetite during nicotine withdrawal is assessed by administering the ligand inhibitor three days following nicotine cessation.

A genetic basis for overeating has been discovered in both mice (e.g., ob/ob) and rats (Zucker strain; fa/fa). These animals offer other models of overeating to assess the efficacy of ligand inhibitors. In particular, Zucker rats are used as subjects. Groups of rats are treated with vehicle or ligand inhibitor on a daily basis over a set time period, such as one week. Subsequent weight gain or food intake is measured. Normal Zucker rats (not genetically obese) serve as controls. Administration of a ligand inhibitor reduces food intake and body weight gain relative to that of normal rats.

In humans, obesity is related not only to overeating, but may also be related to consumption of nutritionally imbalanced diets such as a disproportionately large intake of sweet or fatty foods. (Drewnowski et al., *Am. J. Clin. Nutr.* 46:442, 1987.) Thus, clinical manifestations of appetite regulation are readily detected using controlled experimental diets or cafeteria self-selection protocols which record intake patterns in terms of quantity, meal duration, and choice (Kissileff, *Neurosci. Biobehav. Rev.* 8:129, 1984). In these tests, following a baseline determination for each individual, measurement of food intake or self-selection in the cafeteria environment are measured. Improvement in the context of the treatment of obesity constitutes a weight loss or reduction in food intake exhibited by treated patients as compared to members of a placebo group. Moreover, this strategy has been successful in identifying serotonergic agonists for obesity.

Diseases Associated with Low Levels of CRF

As noted above, the present invention provides methods for treating diseases associated with low levels of CRF through the administration to a patient of a therapeutically effective amount of a ligand inhibitor of a CRF/CRF-BP complex. Such patients may be identified through diagnosis of eating disorders, neuroendocrine disorders, and cognitive disorders, such as Alzheimer's disease. In addition, other conditions associated with decreased CRF levels, such as atypical depression, seasonal depression, chronic fatigue syndrome, obesity, vulnerability to inflammation disease, post-traumatic stress disorder, and psychostimulant withdrawal often present a profile of hypothyroidism and decreased stress system activity which is identified characteristically by a decrease in urinary free cortisol and plasma ACTH. Thus, these diseases and conditions would likely be resolved in part by restoration or potentiation of brain CRF levels (Chrousos and Gold, *JAMA* 267:1244, 1992).

The hallmark of this diverse set of human disease states is dysregulation of the pituitary-adrenal axis with a presumed derangement of brain CRF. Hence, the fact that experimental alternation of CRF/pituitary-adrenal systems in laboratory animals reproduces essential features of the above syndromes, namely behavioral despair (Pepin et al., 1992), exercise fatigue (Rivest and Richard, 1990), obesity (Rothwell, 1989) and hyperarousal associated with psychostimulant withdrawal (Koob et al., 1993; Swerdlow et al., 1991) suggests the broad utility of pharmacotherapies designed to normalize endogenous levels of CRF.

The essential feature of seasonal depression (major depressive disorder with seasonal pattern) is the onset and remission of major depressive episodes at characteristic times of the year. In most cases, the episodes begin in fall or winter and remit in spring. Major depressive episodes that occur in a seasonal pattern are often characterized by prominent anergy, hypersomnia, overeating, weight gain, and a craving for carbohydrates and must persist for a period of at least two weeks during which there is either depressed mood or the loss of interest or pleasure in nearly all activities.

The essential feature of post-traumatic stress disorder is the development of characteristic symptoms following exposure to an extreme traumatic stressor involving direct personal experience of an event that involves actual or threatened death or serious injury to one's own or another's physical integrity. The person's response to the event must involve intense fear, helplessness, or horror. The traumatic event is reexperienced as intrusive recollections or nightmares which trigger intense psychological distress or physiological reactivity. The full symptom picture must be present for more than one month and cause clinically significant distress or impairment in social or occupational functioning.

The essential feature of nicotine withdrawal (nicotine-induced disorder) is the presence of a characteristic withdrawal syndrome that develops after the abrupt cessation of, or reduction in, the use of nicotine-containing products following a prolonged period (at least several weeks) of daily use. Diagnosis of nicotine withdrawal requires identification of four or more of the following: dysphoric or depressed mood, insomnia, irritability or anger, anxiety, difficulty concentrating, restlessness or impatience, decreased heart rate and increased appetite or weight gain. These symptoms must cause clinically significant distress or impairment in social, occupational functioning.

Improvement constitutes either (a) a statistically significant change in the symptomatic condition of a treated individual as compared to a baseline or pretreatment condition on measures pertinent to the disease model; or (b) a statistically significant difference in the symptomatic condition of ligand-inhibitor treated patients and members of a placebo group. Clinical instances of disease exhibit symptoms which are, by definition, distinguishable from normal controls. For depression, several rating scales of depression are used. (See Klerman et al., *Clinical Evaluation of Psychotropic Drugs: Principles and Guidelines*, Prien and Robinson (eds.), Raven Press, Ltd., New York, 1994). One test, the Hamilton Rating Scale for Depression, is widely used to evaluate depression and is also used to assess symptom changes in response to treatment. Other tests and ratings can be found in the DSM-IV manual. For nicotine withdrawal, as well as the other disorders, tests for evaluation of the severity of the disorder can be found in the DSM-IV manual.

Alzheimer's Disease

As noted above, the present invention provides methods for treating Alzheimer's disease ("AD") through the administration to a patient of a therapeutically effective amount of a ligand inhibitor of a CRF/CRF-BP complex. Such patients may be identified through clinical diagnosis based on symptoms of dementia or learning and memory loss which are not attributable to other causes. In addition, patients are also identified through diagnosis of brain atrophy as determined by magnetic resonance imaging.

Decreased levels of CRF are shown to be implicated in Alzheimer's disease. Brains obtained post-mortem from ten individuals with AD and ten neurologically normal controls were chosen for study. Standard areas of frontal pole, parietal pole, temporal pole, and occipital pole were dissected from fresh brain, frozen in dry ice, and stored at $-70°$ C. until they were processed for CRF radioimmunoassay and CRF-BP assay. Formalin-fixed samples of the cerebral cortex and hippocampus were embedded in paraffin and subsequently sectioned and stained with hematoxylin/eosin and silver impregnation. Examination of stained sections from brains of AD patients showed abundant neuritic plaques and neurofibrillary tangles typical of AD, whereas control cases showed none.

Figure 1B:
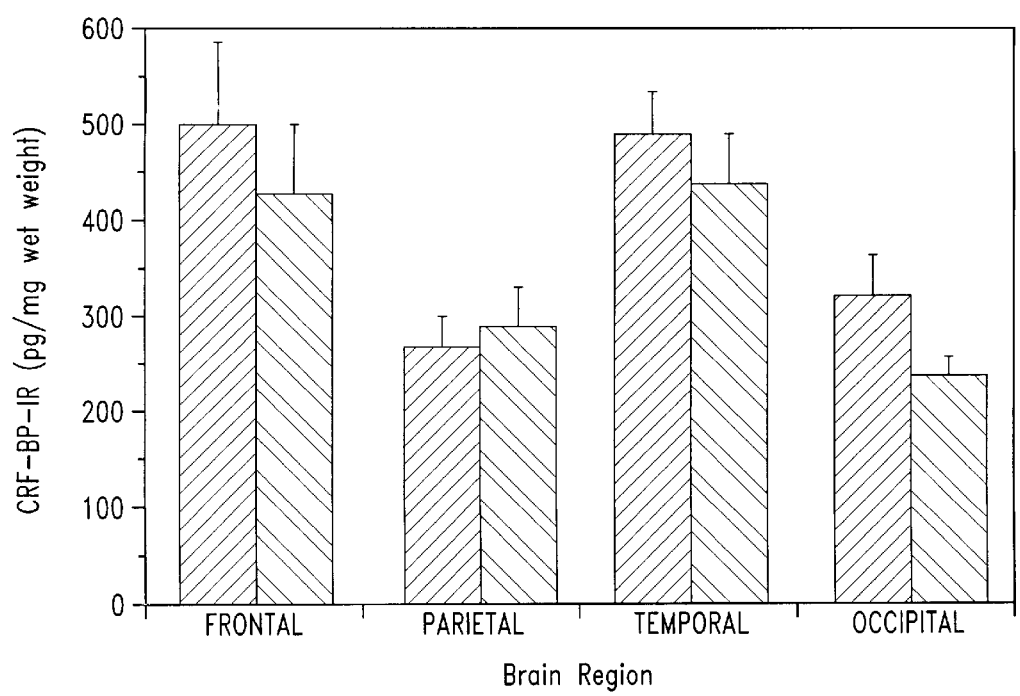

Levels of CRF and CRF-BP in the cerebral cortices of Alzheimer's patients and controls were determined. CRF-BP has previously been identified and characterized in rat brain, sheep brain, and human plasma. In the cerebral cortex of brains studied here, the majority (>85%) of CRF-BP was membrane associated. Pharmacological characteristics of CRF-BP solubilized from human brain membranes from either controls or AD patients showed no differences in binding characteristics to CRF and ligand inhibitors when compared to a recombinant form of the soluble plasma CRF-BP. In brains of Alzheimer's patients, the levels of CRF in the frontal, parietal, and temporal cerebral cortex were dramatically reduced compared to normal brains, but the levels in the occipital cortex were only slightly decreased (FIG. 1A). In contrast, CRF-BP levels were similar in brains of AD patients and normal controls (FIG. 1B). These data provide direct evidence for the presence of CRF-BP in normal and AD brain tissue and suggest that deficits in CRF levels seen in AD may be due to decreased synthesis or increased degradation of CRF rather than neuronal loss. If there is neuronal loss in AD, then CRF-BP may be preferentially localized to non-CRF neurons.

The nature of the interaction of CRF with CRF-BP in human brain tissue was determined by measuring the proportions of CRF complexed to CRF-BP and in the free pool. Using assays specific for total CRF and bound CRF, approximately 40% and 60% of the total CRF were found complexed with CRF-BP in normal and Alzheimer's cerebrocortical extracts, respectively. Furthermore, CRF was bound to CRF-BP in a reversible manner. Moreover, treatment with a CRF-BP ligand inhibitor raised free CRF levels in AD brains to the level found in normal brains.

Several established animal models of Alzheimer's disease which focus on cholinergic deficits are available. The primary role of cholinergic deficits in AD is well established. In AD, there are significant positive correlations between reduced choline acetyltransferase activity and reduced CRF levels in the frontal, occipital, and temporal lobes (DeSouza et al., 1986). Similarly, there are negative correlations between decreased choline acetyltransferase activity and an increased number of CRF receptors in these three cortices (Id.). In two other neurodegenerative diseases, there are highly significant correlations between CRF and choline acetyltransferase activity in Parkinson's disease, but only a slight correlation in progressive supranuclear palsy (Whitehouse et al., 1987).

In rats, anatomic and behavioral studies evidence interactions between CRF and cholinergic systems. First, in some brain stem nuclei, CRF and acetylcholinesterase are co-localized, and some cholinergic neurons also contain CRF. Second, CRF inhibits carbachol-induced behaviors (carbachol is a muscarinic cholinergic receptor antagonist), suggesting that CRF has effects on cholinergic systems (Crawley et al., *Peptides* 6:891, 1985). Treatment with another muscarinic cholinergic receptor antagonist, atropine, results in an increase in CRF receptors (DeSouza and Battaglia, *Brain Res.* 397:401, 1986). Taken together, these data show that CRF and cholinergic systems interact similarly in humans and animals.

An animal model of Alzheimer's disease which focuses on cholinergic deficits is produced by the administration of scopolamine, a non-selective postsynaptic muscarinic receptor antagonist that blocks the stimulation of postsynaptic receptors by acetylcholine. In these animals, memory deficits are readily apparent as measured by passive avoidance or delayed-matching-to-position tests, which distinguish motor or perceptual deficits from amnesia or cognitive enhancing effects of experimental treatments. Thus, the Morris maze and Y-maze tests following scopolamine-induced amnesia are utilized to test memory impairment and subsequent enhancement following administration of ligand inhibitor. In the Morris maze, the design of the experiment is essentially as described above, but is modified to include treatment 30 minutes prior to training on each of days 1 to 3 with an ip injection of scopolamine hydrobromide (0.3 mg/kg). This amnestic dose of scopolamine impairs acquisition and retention of spatial and avoidance learning paradigms in the rat. The anti-amnestic effects of a ligand inhibitor are measured relative to the concurrent control groups who receive or do not receive scopolamine. The effect of the ligand inhibitors on reversal of scopolamine-induced amnesia using the Y-maze is performed similarly to the Y-maze test described above. Modification of this test includes treatment 30 minutes prior to training on days 5 to 10 with an ip injection of scopolamine hydrobromide (0.3 mg/kg). The anti-amnestic effects of a ligand inhibitor administered centrally or systemically are measured relative to concurrent control and scopolamine treated-control groups.

Several tests measuring cognitive behavior in AD have been designed. (See Gershon et al., *Clinical Evaluation of Psychotropic Drugs: Principles and Guidelines*, Prien and Robinson (eds.), Raven Press, Ltd., New York, 1994, p. 467.) One of these tests, BCRS, measures concentration, recent memory, past memory, orientation, and functioning and self-care. The BCRS is designed to measure only cognitive functions. This test, as well as the Weschler Memory Scale and the Alzheimer's Disease-Associated Scale, may be used to determine improvement following therapeutic treatment with ligand inhibition. As noted above, "improvement" in Alzheimer's disease is present within the context of the present invention if there is a statistically significant difference in the direction of normality in the Weschler Memory Scale test, for example, between the performance of ligand-inhibitor treated patients as compared to members of the placebo group or between subsequent tests given to the same patient. In addition, scopolamine-induced amnesia in humans can be used as a model system to test the efficacy of the ligand inhibitors.

Administration of Ligand Inhibitor

As used herein, the terms "pharmaceutically acceptable", "physiologically tolerable" and grammatical variations thereof, as they refer to compositions, carriers, diluents and reagents, are used interchangeably. Preferably, the materials are capable of administration to a mammal without the production of undesirable physiological effects, such as nausea, dizziness, gastric upset and the like.

A ligand inhibitor of a CRF/CRF-BP complex is administered to a patient in a therapeutically effective amount. A therapeutically effective amount is an amount calculated to achieve the desired effect, either increasing the level of free CRF in the brain, improving learning and memory, decreasing food intake, activating CRF neurocircuitry in the brain, treating diseases associated with low levels of CRF in the brain, treating the symptoms associated with Alzheimer's disease, treating obesity, treating atypical depression, treating substance abuse withdrawal, treating post-partum depression, or age-related memory loss. It will be apparent to one skilled in the art that the route of administration may vary with the particular treatment and also with whether a peptide or non-peptide ligand inhibitor is administered. Routes of administration may be either non-invasive or invasive. Non-invasive routes of administration include oral, buccal/sublingual, rectal, nasal, topical (including transdermal and ophthalmic), vaginal, intravesical, and pulmonary. Invasive routes of administration include ICV, intraarterial, intravenous, intradermal, intramuscular, subcutaneous, intraperitoneal, intrathecal and intraocular.

Intracerebroventricular (ICV) injections are performed on animals as follows. Animals are anesthetized with halothane and secured in a KOPF stereotaxic instrument. A guide cannula aimed above the lateral ventricle is implanted and anchored to the skull with two stainless steel screws and dental cement. For injections, a 30 gauge stainless steel cannula attached to 60 cm of PE 10 tubing is inserted through the guide to 1 mm beyond its tip. Two microliters of ligand inhibitor are injected by gravity flow over a one minute period simply by raising the tubing above the head of the animal until flow begins. Procedures for the other routes of administration are well known in the art.

The required dosage may vary with the particular treatment and route of administration. In general, dosages for ligand inhibitors are given to achieve an end concentration approximately 50 to 125 $\mu$g per 1.5 g of brain tissue or 15 to 38 nmoles per 1.5 g of tissue. These treatments are conducted two or three times a week. Treatments may need to be continuous for retention of therapeutic benefit. Patients are monitored by assessing CRF levels in cerebral spinal fluid or in the brain by imaging as described above. In addition, patients are monitored by assessing performance under various tests as described for each of the treatments.

Therapeutic administration is performed under the guidance of a physician, and pharmaceutical compositions contain the ligand inhibitor in a pharmaceutically acceptable carrier. These carriers are well known in the art and typically contain non-toxic salts and buffers. Such carriers may comprise buffers like physiologically-buffered saline, phosphate-buffered saline, carbohydrates such as glucose, mannose, sucrose, mannitol or dextrans, amino acids such as glycine, antioxidants, chelating agents such as EDTA or glutathione, adjuvants and preservatives. Acceptable nontoxic salts include acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The ligand inhibitors being administered under the guidance of a physician will usually be in the form of pharmaceutical composition that contains the ligand inhibitor and a conventional, pharmaceutically-acceptable carrier. Usually, the dosage will be from about 1 to about 1000 micrograms of the ligand inhibitor per kilogram of the body weight of the host animal per day; frequently it will be between about 100 $\mu$g and about 5 mg but may vary up to about 50 mg. Treatment of subjects with these ligand inhibitors can be carried out to alleviate symptoms and correct detrimental manifestations which are characteristic of the relatively low ambient CRF levels which occurs in Alzheimer's disease patients and chronic fatigue syndrome patients. In the former case, treatment improves short and medium term memory. However, for many of these indications including suppression of appetite, it is necessary for the ligand inhibitor to be delivered to the brain and preferably it is coupled with an agent capable of penetrating the blood-brain barrier. Administration by iv, im, or sc injection effects an increase in cortisol level and can effect a lessening of fatigue. Treatment of subjects with these ligand inhibitors can also be carried out to boost the effective biological concentration of free CRF in order to stimulate the human respiratory system by administration to reach the brain. For treatment of conditions in medical emergencies, such as cardiovascular arrest and shock due to substances or pathological agents, an increase in cortisol level can be achieved by administration by iv, im or sc injection. To promote parturition in pregnancy, the ligand inhibitor, optionally with additional hCRF (or an analogue thereof), is administered to cause the concentration of free hCRF in plasma to rise to at least about 250 pmole/liter or preferably to at least about 0.1 ng/ml. It may also be similarly administered to patients afflicted with AIDS who frequently have low levels of cortisol so that such a CRF-BP blocker could elevate ACTH and cortisol.

The following examples are offered by way of illustration and not limitation.

EXAMPLE 1

Synthesis of Representative Ligand Inhibitors of Structure (I)

This example illustrates the synthesis of representative ligand inhibitors of this invention having structure (I).

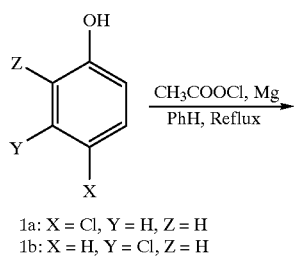

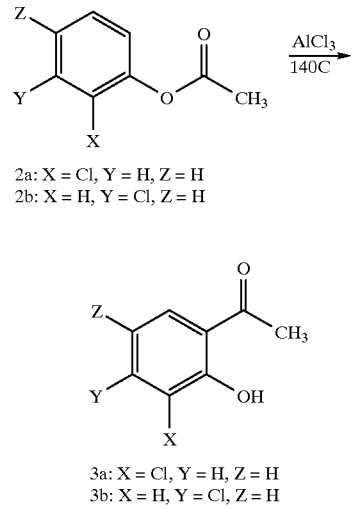

Method A

A mixture of chlorinated phenol (1) (1.0 equiv.), acetyl chloride (1.5 equiv.) and magnesium turnings (0.6 equiv.) in anhydrous benzene was refluxed under a nitrogen atmosphere overnight. The reaction was cooled, filtered and the filtrate was washed with water until a pH 5–6 for the aqueous phase was achieved. The separated organic layer was then dried over $Na_2SO_4$, and concentrated to give the ester product (2) as a colorless oil (88–93%).

Method B

To the ester product (2) (1.0 equiv.) was added aluminum chloride powder (1.5 equiv.) at room temperature with stirring, bubbles formed immediately. The mixture was then heated at about 140° C. for 2 hours. After cooling to room temperature, the hard mass was decomposed with 6N HCl/ice and extracted with ethyl acetate. The organic extracts were washed with water to a pH 5–6 for the aqueous phase, dried over $Na_2SO_4$ and concentrated to give the product mixture. Purification by silica gel chromatography with ethyl acetate/hexane afforded the substituted 2'-hydroxyacetophenones (3).

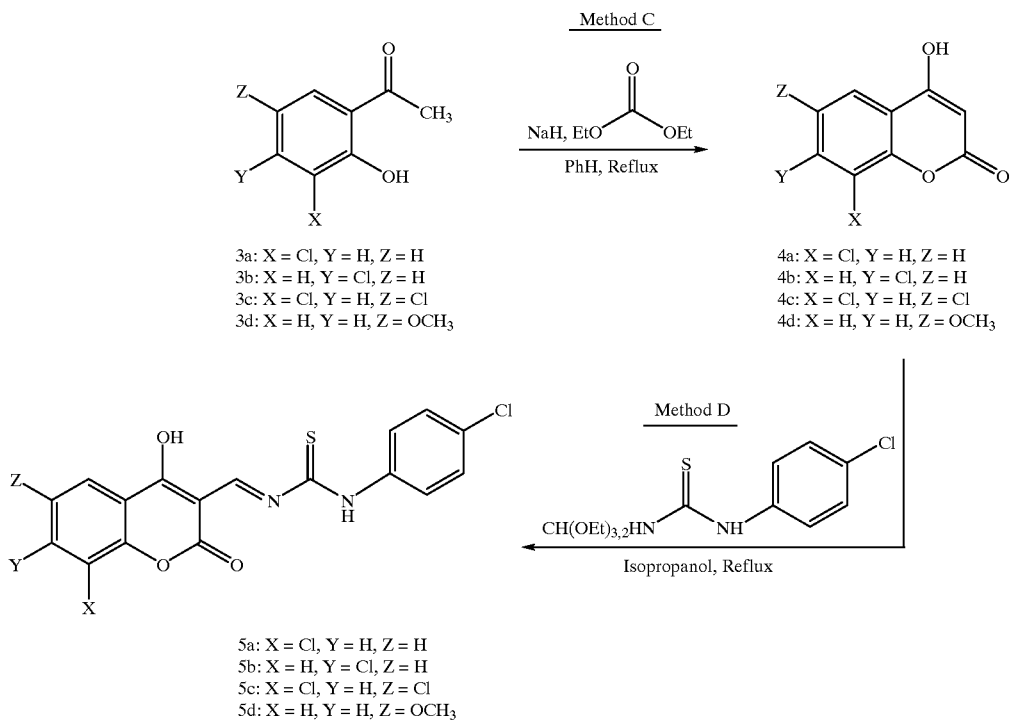

3a: X = Cl, Y = H, Z = H
3b: X = H, Y = Cl, Z = H
3c: X = Cl, Y = H, Z = Cl
3d: X = H, Y = H, Z = OCH$_3$

4a: X = Cl, Y = H, Z = H
4b: X = H, Y = Cl, Z = H
4c: X = Cl, Y = H, Z = Cl
4d: X = H, Y = H, Z = OCH$_3$

5a: X = Cl, Y = H, Z = H
5b: X = H, Y = Cl, Z = H
5c: X = Cl, Y = H, Z = Cl
5d: X = H, Y = H, Z = OCH$_3$

Method C—Option 1 (Method "C-1")

To a stirred mixture of sodium hydride (3.0 equiv., washed free of mineral oil) and diethyl carbonate (10.0 equiv.) in anhydrous benzene was added a solution of compound (3) (1.0 equiv.) in anhydrous benzene, dropwise at room temperature. The reaction mixture was then refluxed under nitrogen atmosphere overnight, cooled to room temperature, then stirred vigorously with 1N NaOH for 3 hours. The separated aqueous layer was acidified with 6N HCl, and the precipitated solid was then extracted with ethyl acetate. The combined organic extracts were washed with water to pH 5–6 for aqueous phase, dried over Na$_2$SO$_4$ and concentrated to give 4-hydroxycoumarin (4) as an off-white solid (50–87%).

Method C—Option 2 (Method "C-2")

To a stirred suspension of sodium hydride (Aldrich, 60% dispersion in mineral oil) (1.2 g, 30.0 mmol) and diethyl carbonate (Aldrich) (5.9 g, 50 mmol) in anhydrous benzene (Aldrich) (100 mL) under a dry nitrogen atmosphere was added dropwise a solution of 5'-fluoro-2'-hydroxy-acetophenone (Aldrich) (1.54 g, 10 mmol) in anhydrous benzene. The mixture was then refluxed under a nitrogen atmosphere overnight. The reaction mixture was cooled and 50 mL 1N NaOH was added. The mixture was stirred at room temperature for 1 hour. The aqueous layer was separated and washed with ether (100 mL×2). The dark solution was acidified to pH 2 with 6N HCl. The white precipitate was collected by filtration, washed with water and dried to afford product (4) (4-hydroxy-6-fluoro-coumarin) as an off-white solid (1.38 g, 7.66 mmol, 77%). 300-MHz $^1$H-NMR (CDCl$_3$) δ 5.79 (s,1H), 7.25–7.28 (m,2H), 7.52 (d,1H). Mass/EI: 179 (M-H).

Method D—Option 1 (Method "D-1")

A solution of substituted 4-hydroxy-coumarin (4) (1.0 equiv), 4-chlorophenylthiourea (1.0 equiv) and triethyl orthoformate (10.0 equiv) in isopropanol was refluxed for 1–2 hours. The yellow solid product was collected by vacuum-filtration, washed with cold isopropanol and further dried under high vacuum to afford product (5) (63–73%).

Method D—Option 2 (Method "D-2")

To a stirred suspension of 4-hydroxy-6-choro-coumarin (1.0 g, 5.0 mmol) and 4-chlorophenylthiourea (Lancaster) (934 mg, 5.0 mmol) in 2-propanol (20 mL) was added triethyl orthoformate (Aldrich) (1.11 g, 7.5 mmol). The mixture was refluxed under nitrogen for 30 minutes. The yellow solid was collected by filtration, rinsed with hexane and dried under vacuum. The product (5) (3-(p-chlorophenyl)thioureidomethylene-4-oxo-6-chloro-coumarin) (Compound No. 1) was obtained as a yellow crystalline solid (1.64 g, 4.2 mmol, 84%). Mass/EI: 391, 393 (M-H).

Method E

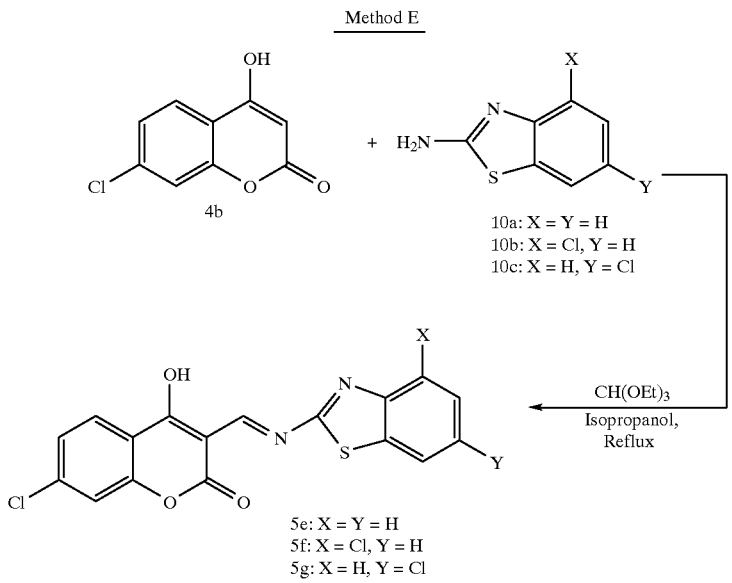

5e: X = Y = H
5f: X = Cl, Y = H
5g: X = H, Y = Cl

Method E

A solution of 4-hydroxy-7-chloro-coumarin (4b) (1.0 equiv.), substituted 2-aminobenzothiozole (10) (1.0 equiv.) and triethyl orthoformate (10.0 equiv.) in isopropanol was refluxed for 1–1.5 hours. The solid product was collected by vacuum-filtration, washed with cold isopropanol and further dried under high vacuum to afford product (5) (77–81%).

EXAMPLE 2

Synthesis of Representative Ligand Inhibitors of Structures (II) and (III)

This example illustrates the synthesis of representative ligand inhibitors of this invention having structures (II) and (III).

Method F

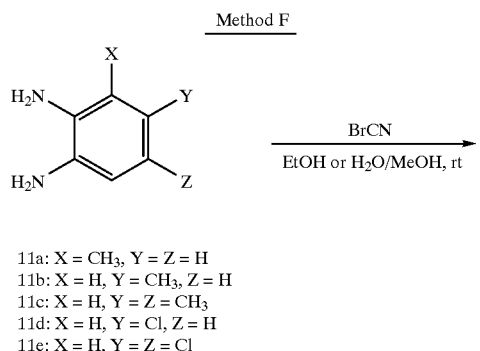

11a: X = CH₃, Y = Z = H
11b: X = H, Y = CH₃, Z = H
11c: X = H, Y = Z = CH₃
11d: X = H, Y = Cl, Z = H
11e: X = H, Y = Z = Cl
11f: X = H, Y = OCH₃, Z = H

-continued

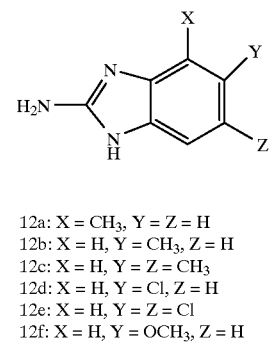

12a: X = CH₃, Y = Z = H
12b: X = H, Y = CH₃, Z = H
12c: X = H, Y = Z = CH₃
12d: X = H, Y = Cl, Z = H
12e: X = H, Y = Z = Cl
12f: X = H, Y = OCH₃, Z = H

Method F

To a suspension of a substituted 1,2-phenylenediamine (11) (1.0 equiv.) in ethanol or methanol/water (1:1) was added cyanogen bromide (1.5–3.0 equiv.) in one portion, the resulting mixture was stirred at room temperature for 2–20 hours. After concentration, the residue was dissolved in water, basified to pH 10–11 with 5N NaOH, then extracted with dichloromethane or ethyl acetate. The combined organic extracts were dried over Na₂SO₄ and concentrated to give substituted 2-aminobenzimidazoles (12).

Method G

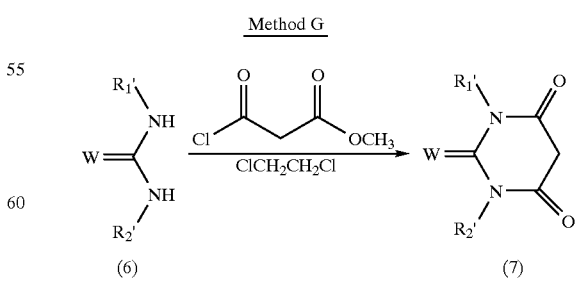

Method G

To a solution of N,N'-dibenzylthiourea (6, W=S) (Lancaster) (6.4 g, 25 mmol) in anhydrous 1,2- dichloroethane (Aldrich) (50 mL) was added dropwise methyl malonyl chloride (Aldrich) (3.75 g, 27.5 mmol) under nitrogen. The solution was refluxed overnight and then cooled to room temperature. The reaction mixture was extracted with 1N NaOH (50 mL×3). The aqueous layers were combined and washed with $CH_2Cl_2$ (50 mL×2). The aqueous solution was then acidified with 4N HCl to pH 2, and extracted with $CH_2Cl_2$ (50 mL×2). The organic layers were combined, washed with Brine solution, dried under a magnesium sulfate, filtered and concentrated to afford a yellow oil which solidified overnight. The product (7) was obtained as a yellow solid (3.71 g, 11.4 mmol, 46%). 300-MHz $^1$H-NMR ($CDCl_3$) δ 3.84 (s,2H), 5.61 (s,4H), 7.27–7.35 (m,10H). Mass/EI: 323 (M-H).

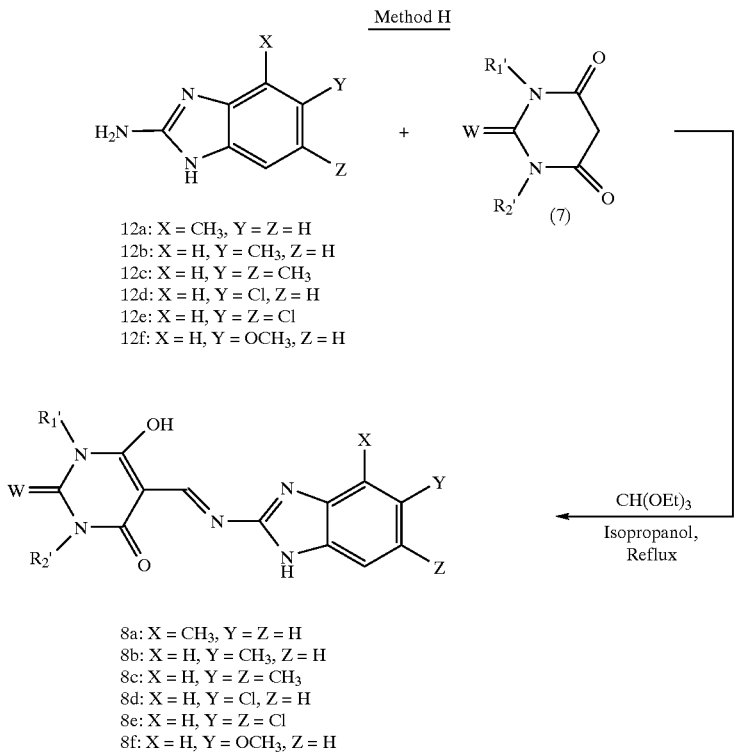

Method H

A solution of 1,3-diethyl-2-thiobarbituric acid (7, W=O) (1.0 equiv.), substituted 2-aminobenzimidazole (12) (1.0 equiv.) and triethyl orthoformate (10.0 equiv.) in isopropanol was refluxed to 1–4 hours. The solid product was collected by vacuum-filtration, washed with cold isopropanol and further dried under high vacuum to afford the final product (8) (59–88%).

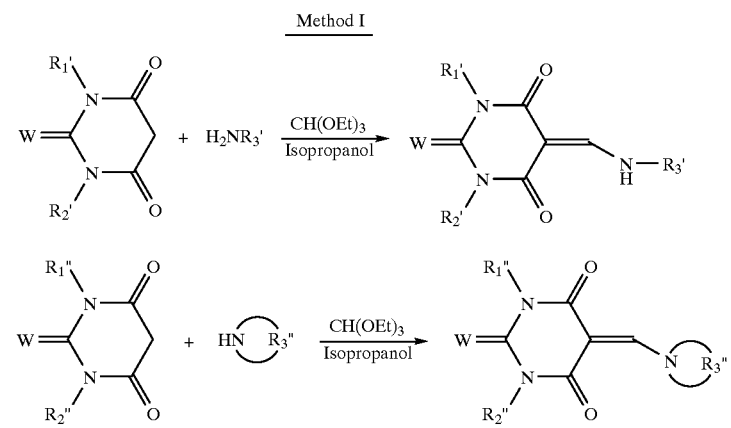

Method I

Using a Hewlett-Packard Prep Station G1292A, compounds of structure (8) and (9) were prepared. Into a reaction vial containing 1 of 3 thiobarbituric acids (W=S; the oxygen analog, where W=O, could be used as well), $R_1'=R_2'=$ methyl, phenyl or ethyl (0.05 mM, 1 equiv.) and a suitable amine (0.075 mM, 1.5 equiv.), was added 0.5 mL of isopropanol and triethylorthoformate (0.075 mL, 1.5 equiv.). The resulting solution was mixed in a mechanical mixer for 2 minutes and then heated at 82° C. for 1 hour. The solution was cooled and the resulting solid was collected by hand decanting each reaction vial. The solid was then washed with isopropanol and dried under vacuum yielding product (8) or (9).

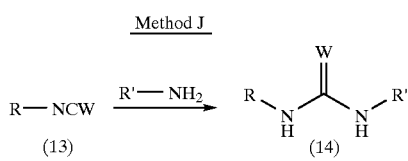

Method J

Method J

This method provides a synthesis of an intermediate useful in preparing components of the invention. To a stirred solution of 1-naphthylthiocyanate, R=1-naphthyl (13) (Aldrich) (555 mg, 3.0 mmol) in anhydrous acetone (Aldrich) (15 mL) was added ammonia, R'=H (Aldrich) (2.0M solution in methyl alcohol) (9 mL, 18 mmol). The solution was stirred at room temperature for 30 minutes. Concentration of the reaction mixture at reduced pressure yielded the product, 1-naphthylthiourea (14) as a pale brown solid (552 mg, 2.7 mmol; 91%). 300-MHz $^1$H-NMR (DMSO-d6) δ 7.47–7.58 (m, 4H), 7.84–7.95 (m, 3H), 9.76 (s, 1H). Mass/PI: 203 (m+H). Compounds (13) of structure R—NCO (W=O) can be used as well in this method.

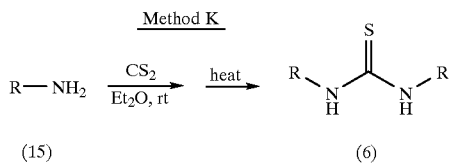

Method K

Method K

To a solution of primary amines (15) (1.5 equiv.) in diethyl ether was added dropwise carbon disulfide (1.0 equiv.) at rt. After stirring for 30 minutes, salt intermediates were obtained in the form of either white solid or colorless oil. After filtration or evaporation, the salt intermediates were heated slowly on an oil bath and kept at the melting point temperature for 15 minutes with stirring (or refluxed if the salt is oil or the amine has low boiling point). After cooling, the products (6) were crystallized from ethanol or obtained as oil after solvent removal (38–99%).

The products (6) can be used according to Method G to prepare compounds of structure (II) according to the invention.

EXAMPLE 3

Representative Ligand Inhibitors

Representative ligand inhibitors of this invention made according to the methods of Examples 1 and 2 are disclosed in Table 18. In Table 18, the compound number, method of preparation and analytical data are presented.

TABLE 18

Representative Compounds

| Cpd. No. | Method | Mass (M-H) |
| --- | --- | --- |
| 1 | D-2, E | 391, 393 |
| 2 | D-2, E | 425, 427, 429 |
| 3 | D-2, E | 387, 389 |
| 4 | D-2, E | 425, 427, 429 |
| 5 | D-2, E | (M-H+MeOH) 403, 405 |
| 6 | D-2, E | 425, 427 |
| 7 | D-2, E | 459, 461, 463, 465 |
| 8 | D-2, E | 357, 359 |
| 9 | D-2, E | 449, 451 |
| 10 | D-2, E | 439, 441 |
| 11 | D-2, E | 382, 384 |
| 12 | D-2, E | 402, 404 |
| 13 | D-2, E | 407, 409 |
| 14 | D-2, E | 371, 373 |
| 15 | D-2, E | 385, 387 |
| 16 | D-2, E | 549, 551 |
| 17 | D-2, E | 523, 525 |
| 18 | D-2, E | 407, 409 |
| 19 | D-2, E | 433, 435 |
| 20 | D-2, E | 433, 435 |
| 21 | D-2, E | 373, 375 |
| 22 | D-2, E | 363, 365 |
| 23 | D-2, E | 349, 351 |
| 24 | D-2, E | 321, 323 |
| 25 | C-2, D-2, E | 409 |
| 26 | C-2, D-2, E | 371, 373 |
| 27 | D-2, E | 399, 401 |
| 28 | D-2, E | 323, 325 |
| 29 | D-2, E | 407, 409 |
| 30 | D-2, E | 407, 409 |
| 31 | C-1, E | 391, 393, 395 |
| 32 | C-1, E | 425, 427, 429 |
| 33 | C-1, E | 387, 389 |
| 34 | C-1, E | 391, 393, 395 |
| 35 | D-2, E | 355, 357 |
| 36 | D-2, E | 389, 391 |
| 37 | D-2, E | 389, 391 |
| 38 | D-2, E | 338, 340 |
| 39 | D-2, E | 369, 371 |
| 40 | D-2, E | 385, 387 |
| 41 | D-2, E | 352, 354 |
| 42 | C-2, D-2, E | 373, 375 |
| 43 | C-1, E | 355, 357 |
| 44 | C-1, E | 389, 391, 393 |
| 45 | C-1, E | 389, 391, 393 |
| 46 | D-2, E | 305, 307 |
| 47 | D-2, E | 340, 342 |
| 48 | I | 395, 397 |
| 49 | I | 463, 465, 467 |
| 50 | I | 391 |
| 51 | I | 361 |
| 52 | I | 367, 369 |
| 53 | I | 519, 521 |
| 54 | I | 423, 425 |
| 55 | I | 407, 409 |
| 56 | I | 419, 493 |
| 57 | I | — |
| 58 | H | 342 |
| 58-1 | H | 417 |
| 59 | H | 359 |
| 59-1 | H | 435 |
| 60 | H | 293, 295 |
| 61 | H | 377, 379 |
| 62 | H | 356 |
| 63 | H | 438 |
| 64 | H | 314 |
| 65 | H | 365, 367 |
| 66 | H | 466 |
| 67 | H | 517, 519 |

TABLE 18-continued

Representative Compounds

| Cpd. No. | Method | Mass (M-H) |
|---|---|---|
| 68 | H | 370 |
| 69 | H | 421, 423 |
| 70 | H | 454 |
| 71 | H | 505, 507 |
| 72 | H | 373 |
| 73 | H | 389 |
| 73-1 | H | — |
| 74 | H | 393, 395 |
| 75 | H | 393, 395 |
| 75-1 | H | 449 |
| 76 | H | 389 |
| 76-1 | H | 465 |
| 77 | H | 377 |
| 78 | H | 437, 439 |
| 79 | H | 404 |
| 80 | H | 427 |
| 81 | H | 387 |
| 82 | H | 404 |
| 83 | H | 354 |
| 84 | H | 405, 407 |
| 85 | H | 370 |
| 85-1 | H | 446 |
| 86 | H | 356 |
| 86-1 | H | 431 |
| 87 | H | 356 |
| 88 | H | 376, 378 |
| 89 | H | 410, 412, 414 |
| 90 | H | 372 |
| 91 | H | 430 |
| 92 | H | 458 |
| 93 | H | 541 |
| 94 | H | 494 |
| 95 | H | 545, 547 |
| 95-1 | H | — |
| 96 | H | 522 |
| 97 | H | 506 |
| 97-1 | H | 522 |
| 98 | I | 342 |
| 99 | I | 466 |
| 100 | I | 370 |
| 101 | I | 324 |
| 101-1 | I | 400 |
| 102 | I | 448 |
| 103 | I | 352 |
| 104 | I | 378 |
| 104-1 | I | 454 |
| 105 | I | 502 |
| 106 | I | 406 |
| 107 | I | 395 |
| 108 | I | 519 |
| 109 | I | 423 |
| 110 | I | 310 |
| 110-1 | I | 386 |
| 111 | I | 434 |
| 112 | I | 338 |
| 113 | I | 409 |
| 114 | I | 437 |
| 115 | I | 494 |
| 116 | I | 398 |
| 117 | I | 323 |
| 117-1 | I | 400 |
| 118 | I | 447 |
| 119 | I | 351 |
| 120 | I | 447 |
| 121 | I | 690 |
| 122 | I | 594 |
| 123 | I | 554 |
| 124 | I | 458 |
| 125 | I | 385 |
| 126 | I | 509 |
| 127 | I | 413 |
| 128 | I | 365 |
| 129 | I | 489 |
| 130 | I | 393 |
| 131 | I | 491 |
| 131-1 | I | 567 |
| 132 | I | 615 |
| 133 | I | 519 |
| 134 | I | 450 |
| 135 | I | 354 |
| 136 | I | 311 |
| 137 | I | 435 |
| 138 | I | 339 |
| 139 | I | 387 |
| 140 | I | 511 |
| 141 | I | 415 |
| 142 | I | 400 |
| 143 | I | 524 |
| 144 | I | 428 |
| 145 | I | 413 |
| 146 | I | 537 |
| 147 | I | 441 |
| 148 | I | 338 |
| 149 | I | 462 |
| 150 | I | 366 |
| 151 | I | 516 |
| 152 | I | 475 |
| 153 | I | 567 |
| 154 | I | 507 |
| 155 | I | 483 |
| 156 | I | 427 |
| 157 | I | 459 |
| 158 | I | 411 |
| 159 | I | 567 |
| 160 | I | 475 |
| 161 | I | 462 |
| 162 | I | 475 |
| 163 | I | 490 |
| 164 | I | 506 |
| 165 | I | 627 |
| 166 | I | 627 |
| 167 | I | 519 |
| 168 | I | 487 |
| 169 | I | 383 |
| 170 | I | 339 |
| 171 | I | 367 |
| 172 | I | 377 |
| 172-1 | I | — |
| 173 | I | 480 |
| 174 | I | 384 |
| 175 | I | 335 |
| 176 | I | 363 |
| 177 | I | 360, 362 |
| 178 | I | 346 |
| 179 | I | 307 |
| 180 | I | 335 |
| 181 | I | 432 |
| 182 | I | 389 |
| 182-1 | I | 467 |
| 183 | I | 513 |
| 184 | I | 417 |
| 185 | I | 356 |
| 186 | I | 342 |
| 187 | I | 466 |
| 188 | I | 370 |
| 189 | I | 342 |
| 190 | I | 466 |
| 190-1 | I | 420 |
| 191 | I | 370 |

EXAMPLE 4

Ligand—Immunoradiometric Assay (LIRMA) to Assay for Ability of Ligand Inhibitor Displacement of CRF from CRF-BP The assay is performed in 600 µl polypropylene microfuge tubes or a 96-well plate. First, 50 µl of a 250 ng/ml of purified recombinant CRF-BP is added to 150 µl of PBS binding buffer (50 mM sodium phosphate, 0.15M NaCl, and 0.02% NP-40). Next, $^{125}$I-h/r CRF at a final concentration of 200 pM and 50 µl of a 10–100 µM concentration of the ligand inhibitor are added and incubated for 1 hour at room temperature. To the reaction, 50 µl of anti-CRF-BP antibody, 5144, diluted 1:1000 with assay buffer is added to each tube and allowed to bind for a further 1 hour at room temperature. The total volume in all tubes is adjusted to 300 µl with assay buffer. Bound complexes are precipitated by the addition of 200 µl of preprecipitated goat anti-rabbit (GAR) second antibody at 1:20 in 1% normal rabbit serum, 4% PEG, 50 mM sodium phosphate, 0.1% sodium azide, followed by incubation for 1 hour at room temperature. The antibody-bound $^{125}$I-CRF precipitate is then collected by centrifugation (3000×g) at 4° C. for 20 minutes in a Beckman GS-15R centrifuge. Using a Beckman Biomer 1000 robotic workstation, the tubes are aspirated and washed once with 600 µl of PBS plus 0.02% NP-40. Tubes containing the pellets are then transferred to 12×74 mm counting tubes and counted in a gamma counter.

Inhibitory binding affinity constant ($K_i$) values are determined using the method of Munson et al., *Anal. Biochem.* 107:220, 1980.

EXAMPLE 5

Detergent Phase Separation to Assay for the Ability of Ligand Inhibitor Displacement of CRF from CRF-BP Recombinant human CRF-BP at 200 ng/ml is incubated in binding buffer (phosphate buffered saline, pH 7.4/0.02% NP-40) with radiolabeled $^{125}$I-h/r CRF (80 pM) for 2 hours at room temperature. Following incubation, bound and free CRF are separated by the addition of a 1:10 dilution of Triton X-114™ in assay buffer octylphenoxypolyethoxyethanol (SIGMA). Triton X-114™ is insoluble in water at room temperature and in aqueous solution can be separated into a detergent phase. After addition of the Triton X-114™, the tube is vortexed and immediately centrifuged at room temperature at 12,000×g for 5 minutes. The detergent phase is found at the bottom of the tube while the aqueous phase remains at the top. CRF, which as amphiphilic alpha helices, segregates to the detergent phase. However, when CRF is bound to CRF-BP, the CRF/CRF-BP complex remains in the aqueous phase. Thus, a 50 µl aliquot of the aqueous phase is transferred to a 12×74 mm plastic tube and counted. The amount of radioactivity left in the supernatant is determined.

EXAMPLE 6

ACTH Release Assay for Free CRF

Four rats are killed by decapitation and the anterior pituitary glands are removed. The anterior pituitary glands are washed 6 times with sterile HEPES buffer and transferred to 20 ml of collagenase solution (4 mg/ml). The pituitaries in collagenase are then transferred to a 25 ml Bellco dispersion flask and stirred for 30 minutes at 37° C. After 30 minutes, the pituitary cell suspension is then triturated by drawing the pituitaries through a 10 ml pipette and incubated for 30 minutes more before more trituration. The cell suspension is incubated for a further 45 minutes and the partially dispersed cells are transferred to a sterile 50 ml tube and centrifuged at 4000 rpm for 4 minutes. The cell pellet is reconstituted in 10 ml of neuraminidase (8 µg/ml) and vortexed. The suspension is placed in a water bath for 9 minutes, vortexed again for 4 minutes and centrifuged again. The supernatant is poured off and the cell pellet is reconstituted in 25 ml of BBM-P (250 ml BBM-T plus 5 ml of 2% fetal calf serum) by vortexing. The cells are collected by centrifugation, and finally the suspension is reconstituted in 22 ml of BBM-P. The cells are then plated at a density of 50–100,000/well in a 48 well plate and incubated in a humidified $CO_2$ chamber for 2 days. On the day of assay, the cells are washed once with BBM-T in preparation for stimulation with the various relevant analogues.

The cells are stimulated with a maximally stimulating dose of h/rCRF (1 nM) in the presence and absence of a blocking concentration of CRF-BP (5 nM). This concentration of CRF-BP reduces the amount of ACTH released from the pituitary cells by binding to h/rCRF. The reduction is expressed as a fraction of the amount of ACTH released by 1 nM CRF in the absence of CRF-BP. The CRF-BP (5 nM), which is bound to h/rCRF (1 nM), is incubated with a range of concentrations of ligand inhibitors (e.g., typical concentrations for the ligand inhibitors range from 0.1–1000 nM). The ligand inhibitor binds to CRF-BP and displaces CRF from the complex resulting in a dose-dependent reversal of the inhibition of h/rCRF induced-ACTH secretion by CRF-BP. The potency of the CRF-BP ligand is expressed as a fraction of ACTH release obtained by stimulation with 1 nM CRF alone.

EXAMPLE 7 cAMP Production Assay to Measure Free CRF

The assay for detection of CRF-stimulated adenylate cyclase activity is carried out as previously described (Battaglia et al., 1987) with minor modifications. The standard assay mixture contains 2 mM L-glutamine, 20 mM HEPES, 1 mM IBMX (isobutylmethyl xanthine) in DMEM buffer. In stimulation studies, cells that have been transfected with a clone encoding CRF receptor are plated in 24 well plates and incubated for 1 hour at 37° C. with various concentrations of CRF-related and unrelated peptides. Following the incubation, the media is aspirated, the wells rinsed once gently with fresh media and aspirated. The amount of intracellular cAMP is determined after lysing the cells in 300 µl of a solution of 95% ethanol and 20 mM HCl at 20° C. for 16–18 hours. The lysate is transferred into 1.5 ml Eppendorf tubes, the wells are washed with an additional 200 µl of EtOH/HCl, and the wash is pooled with the lysate. The lysates are lyophilized and resuspended in 500 µl of sodium acetate buffer, pH 6.2. cAMP is measured with a single antibody kit from Biomedical Technologies Inc. (Stoughton, Mass.). For the functional assessment of CRF receptor antagonists, a single concentration of CRF or related peptides causing 80% stimulation of cAMP production is incubated along with various concentrations of competing compounds ($10^{-12}$ to $10^{-16}$M). The incubation and measurement conditions for cAMP are performed as described.

EXAMPLE 8

Two-Site ELISA to Measure CRF Levels

A. Preparation of brain tissue samples

Autopsy samples are weighed and homogenized in 5 ml of 10% sucrose. One ml of each sample is centrifuged at 10,000×g for 10 minutes at room temperature and the resultant membrane pellets are reconstituted in SPEA (50 mM sodium phosphate pH 7.4, 0.1M NaCl, 25 mM EDTA, 0.1% sodium azide, containing 0.25% bovine serum albumin (BSA) and 1% NP-40). Eight hundred microliters of cerebral cortex homogenate (in 10% sucrose) is further extracted by the addition of 200 μl of TTBS (Tris-buffered saline with 0.5% Tween –20, 1% NP-40, 1% BSA) followed by vortexing for 1 minutes. The sample is centrifuged at 10,000×g for 10 minutes at room temperature. The resultant supernatant is kept for analysis of "total CRF," "bound CRF" (i.e., CRF bound to CRF-BP) and "free CRF" using a two-site CRF ELISA.

B. Measurement of total CRF

Briefly, ELISA plates are coated for 2 hours at 37° C. with protein G-purified sheep anti-CRF antibody (20 μg/ml) diluted in 50 mM sodium bicarbonate buffer, pH 9.5. Plates are washed once with TTBS and blocked with 1% casein in TBS for 1 hour at room temperature. One hundred microliters of the samples or standard are added to each well and allowed to bind at room temperature. Plates are washed five times with TTBS. RC-70 rabbit anti-human CRF antibody (diluted 1:1000 in TTBS/1% BSA) is added. Following incubation for 1 hour at room temperature, plates are washed five times with TTBS buffer and then exposed to horseradish peroxidase conjugated-goat anti-rabbit (GAR) second antibody for 1 hour at room temperature. Plates are finally washed five times with TTBS and developed by the addition of 100 μl of TMB microwell peroxidase substrate solution (Kikegaard and Perry Laboratories, Inc.). Absorbance at 450 nM is determined.

C. Measurement of bound CRF

Bound CRF is determined by capture of the CRF/CRF-BP complex in wells which had been pre-coated with an anti-human CRF-BP monoclonal antibody (5 μg/ml of antibody in 50 mM sodium bicarbonate buffer, pH 9.5) followed by detection of the bound CRF with RC-70 anti-human CRF antibody essentially as described for the total CRF ELISA.

D. Measurement of free CRF

Free CRF is measured in the supernatant following capture of the bound complex by the anti-CRF-BP monoclonal antibody. Following binding of sample material, the supernatant is removed to a new ELISA plate coated with protein G-purified sheep anti-CRF antibody. The assay is then performed as described for determining total CRF levels.

EXAMPLE 9

Screening for Ligand Inhibitors

Candidate ligand inhibitors may be screened for their ability to displace CRF from CRF/CRF-BP complex. A suitable assay, such as ACTH release from cultured pituitary cells (see Example 6) or two-site LIRMA (see Example 4), is used to measure free CRF and CRF-BP levels, respectively.

In the LIRMA assay, generally the procedure from Example 4 is followed. The ligand inhibitor at a 10 μM concentration is added to the reaction along with the $^{125}$h/r CRF. If the candidate ligand inhibitor displaces CRF from CRF-BP, the pellets will contain less radioactivity in comparison to controls in which no ligand inhibitor is added. Candidate ligand inhibitors are re-screened using a 6 point-dose curve. IC-50 values are calculated.

Figure 2:
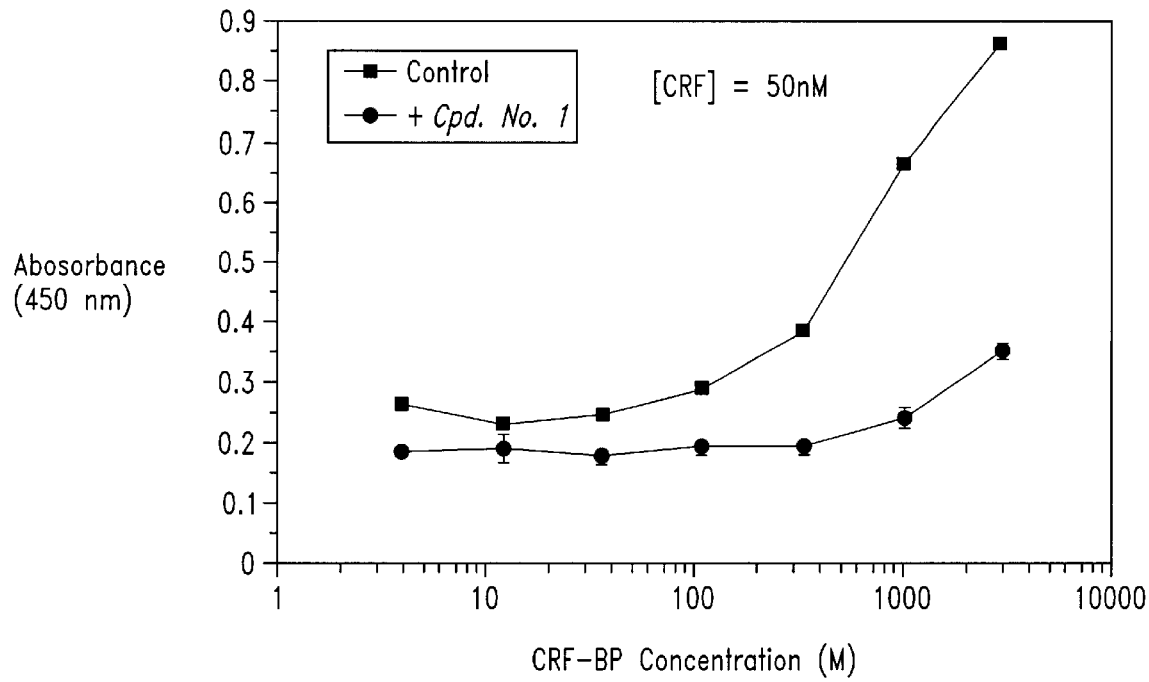
FIG. 2 is a graph showing that a representative ligand inhibitor, Compound No. 1, inhibits the formation of CRF/CRF-BP complexes. An ELISA was performed with a fixed amount of CRF and ligand inhibitor in the presence of increasing concentration of CRF-BP.

Representative ligand inhibitors of this invention have been screened by LIRMA for binding to human recombinant CRF-BP. For example, Compound No. 1 has been found to inhibit the formation of the CRF/CRF-BP complex in vitro (FIG. 2).

Figure 3:
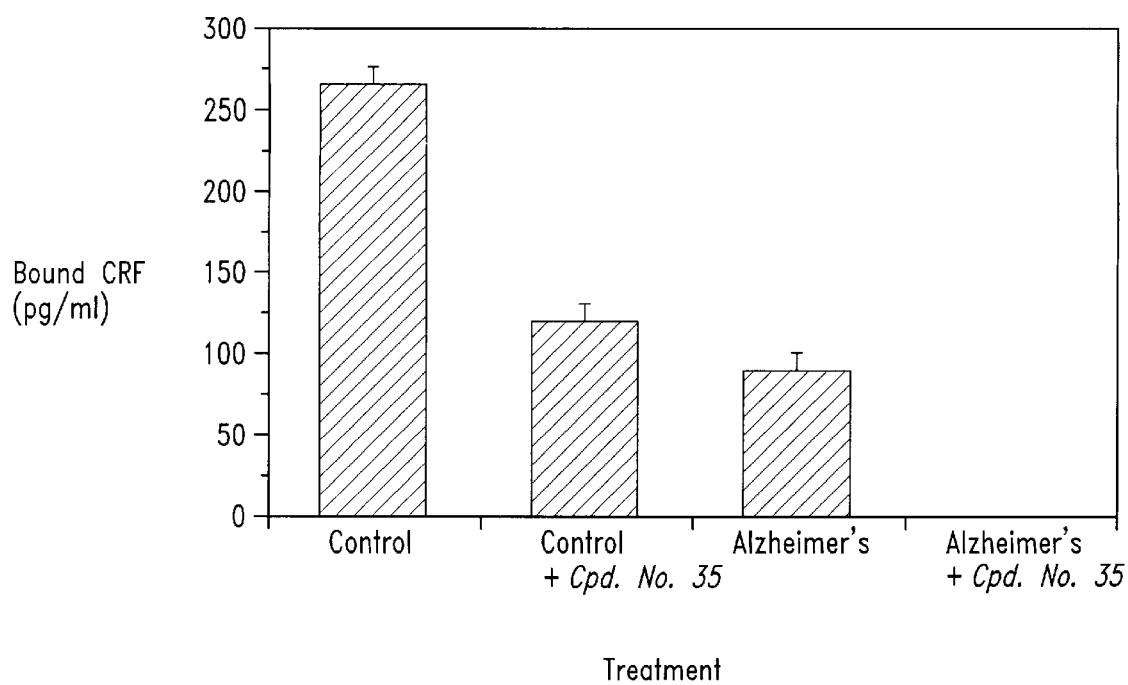
FIG. 3 is a graph displaying the results of ELISAs testing the ability of a representative ligand inhibitor, Compound No. 35, to displace endogenous CRF from CRF-BP in brain tissue from Alzheimer's disease patients and normal controls.

Another ligand inhibitor, Compound No. 35, was tested for its ability to inhibit CRF/CRF-BP complexes in NP-40 solubilized human cerebrocortical brain tissue obtained postmortem from controls and Alzheimer disease patients. Briefly, 0.1–0.5 g of brain tissue was homogenized in phosphate-buffered saline containing 0.2% NP-40. The homogenate was clarified by centrifugation at 3000×g for 10 minutes. Supernatants were assayed by ELISA for the formation of CRF/CRF-BP complex in the presence or absence of Compound No. 35. As shown in FIG. 3, Compound No. 35 inhibits formation of CRF/CRF-BP complexes in brains of controls and Alzheimer's disease patients.

EXAMPLE 10

Treatment with Ligand Inhibitor

Five cerebrocortical samples from Alzheimer's patients and five samples from age-matched, normal controls are prepared as in Example 8 and pooled. Levels of total CRF, bound CRF, and free CRF are measured as described in Example 8, showing 40% of the total CRF complexed to CRF-BP in brain extracts from normal individuals and 60% complexed in brain extracts from Alzheimer's patients. The effect of a ligand inhibitor to displace bound CRF is assessed after monoclonal capture of the CRF/CRF-BP complex. Displaced free CRF is measured in the supernatants remaining after CRF-BP monoclonal antibody capture by CRF ELISA. Treatment of brain tissues with the ligand inhibitor causes release of all bound CRF in both Alzheimer's and control tissues. Moreover, treatment of the Alzheimer's disease cerebral cortex with the ligand inhibitor replenishes the free CRF levels to those in age-matched controls.

EXAMPLE 11

Morris Water Maze Test

The Morris Water Maze Test is a simple spatial learning task that requires a minimal amount of stress and experience. No motivational constraints such as shock or food deprivation are necessary. The animal is placed in tepid water, which is opaque due to the addition of milk powder. The latency time to find a hidden platform is monitored. The animals learn the location of the platform relative to visual cues located within the maze and the testing room; this learning is referred to as place learning. This test is particularly sensitive to manipulations of the hippocampus, a critical brain area involved in spatial learning in animals and memory consolidation in humans.

The apparatus used in this test is a pool (46.4 cm in diameter, 45.7 cm high) filled to a depth of 23 cm with opaque water (22° C.–25° C.). The top of a weighted target platform, 10 cm in diameter, is located 1–2 cm beneath the water surface. Four equal quadrants of the pool are distinguished by designs located on the inner surface. The animal is placed into a designated quadrant of the tank and the time to approach and ascend the hidden platform is measured; the location of subject placement and platform remain constant throughout the experiment. After climbing on top of the platform, the animal is allowed to rest for 20 sec. Subjects that do not find the platform within 60 sec are placed onto the platform and allowed to rest for 20 sec.

Figure 4A:
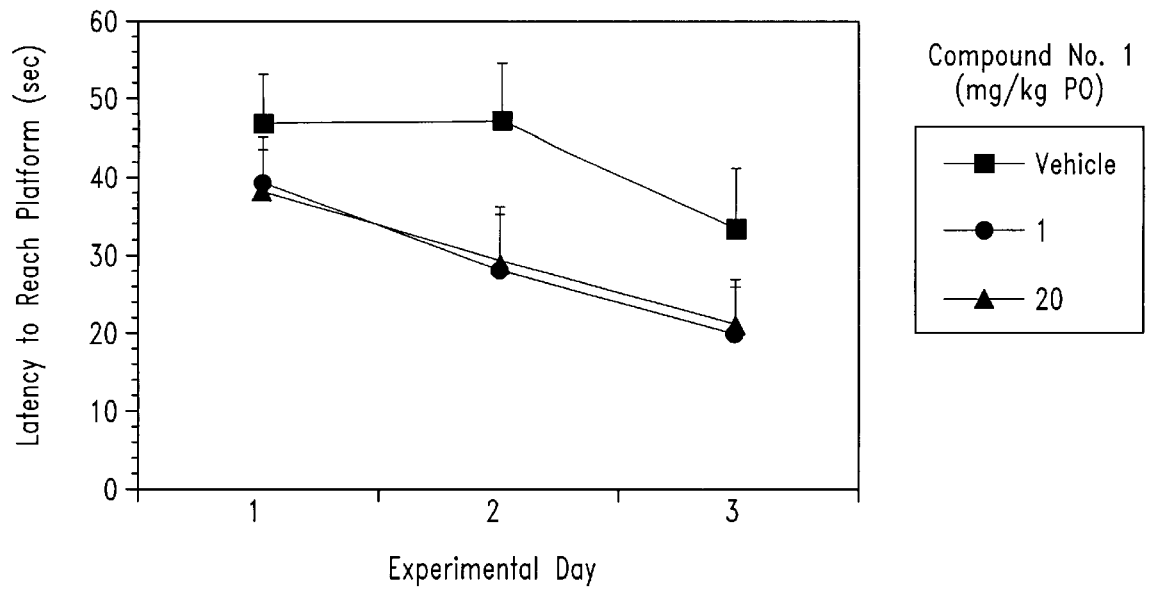
FIGS. 4A and 4B are graphs displaying the results of Morris water maze testing. Rats were administered vehicle or a representative ligand inhibitor of this invention prior to testing. Following training, rats were tested on days 1, 2 and 3. The results of these experiments for Compound No. 1 are shown in FIG. 4A and for Compound No. 153 in FIG. 4B.
Figure 4B:
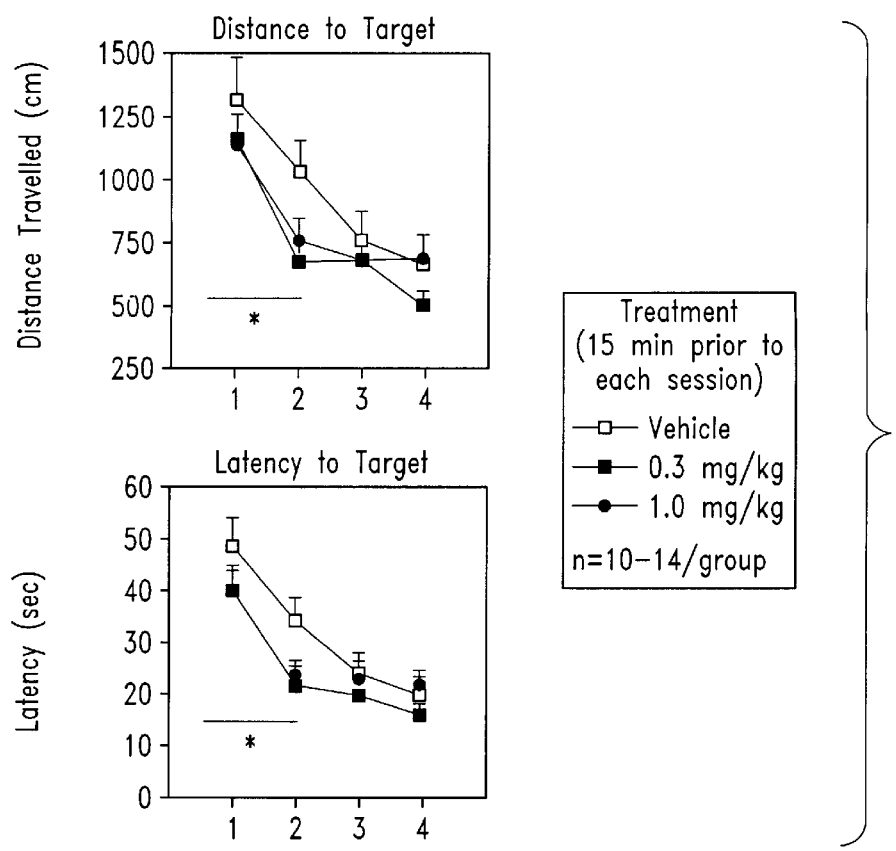

Rats were treated by oral administration with either vehicle or 1 or 20 mg/kg of either Compound No. 1 or Compound No. 153 15 minutes prior to testing. The latency time to reach the platform in the Morris water maze was recorded for each group. As shown in FIGS. 4A and 4B, Compound Nos. 1 and 153 improved performance at each time interval.

EXAMPLE 12

Y-Maze Visual Discrimination Test

The Y-Maze visual discrimination test is a learning test using positive reinforcement to study learning with minimal stress to the animals. Subjects are meal deprived and fed only after the training session; animals have the option of not responding, but do so in most cases because the positive reinforcing properties of the food pellets, which rats prefer to regular chow.

The Y-maze contains three arms of equal length (61 cm long, 14 cm wide, 30 cm high). One arm is used as a start box and is separated from the other two goal arms by guillotine doors which are manually operated. The vertical surface at the ends of the two distal arms is equipped with an eight watt electric bulb. On the first day of training, rats, which have been food-deprived to 80% body weight, are allowed to explore the maze for 5 minutes with two food pellets (45 mg Noyes) available at the end of each goal arm. On the second day, each rat was allowed one trip down each of the goal arms which are baited with pellets. On the third day, rats receive six spaced trials in squads of three animals where one goal arm was closed at the choice point and two 45 mg pellets are available in the open goal box, but no discriminative visual stimulus is provided (light off). The open arm alternates from left to right over the six trials, as well as from subject to subject. On days 4–10, both goal arms are open and the light at the end of one goal arm is illuminated. Ten trials are run daily, again in squads of three so that the intertrial interval is about 90 sec. Subjects are fed a 15 g portion of laboratory chow in the home cage daily at the conclusion of training.

On days 4–10, ICV administration of ligand inhibitor is given immediately prior to testing. Groups of 7–9 rats receive either 0 (control) or 5–25 kg of the ligand inhibitor. Percent correct responses are recorded. Rats receiving 5 and 25 µg of the ligand inhibitor will show better performance than rats receiving 0 or 1 µg of the ligand inhibitor.

EXAMPLE 13

Elevated Plus-Maze Test

The Elevated plus-maze test predicts how animals respond to an approach-avoidance situation involving an exposed, lighted space versus a dark, enclosed area. In the maze, both spaces are elevated off the ground and constitute two runways intersecting in the form of a plus sign. This type of approach-avoidance situation is a classical test of "emotionality" and is very sensitive to treatments that produce disinhibition (such as sedative or hypnotic drugs) and stress. No motivational constraints are necessary and the animal is free to remain in the dark or venture out onto the open arms.

The elevated plus-maze apparatus has four arms (50 cm long, 10 cm wide) situated at right angles to each other and elevated from the floor (50 cm). Two of the arms are enclosed with walls (40 cm high) and two arms have no walls (open arms). Subjects are placed individually into the center of the maze and allowed free access to all four arms for a 5 minute testing period. The time spent in each arm is recorded automatically by photocell beams and a computer interface.

Groups of 7–10 rats receive ICV injections of the ligand inhibitor. For purposes of comparison, rats also receive 0 or 0.1–25 µg of h/rCRF (1–41). Doses of 1 and 25 µg of h/rCRF (1–41) will show significantly more time on the open arms, indicating increased anxiety. In marked contrast, memory-enhancing doses of a ligand inhibitor of this invention, as well as doses two- to five-fold higher (50–125 mg), will not alter performance or produce overt behavioral alterations comparable to h/rCRF (1–41). h/rCRF (1–41) is known to be a CRF-receptor agonist. Therefore, this data will demonstrate a clear-cut functional dissociation of the efficacious cognitive enhancing and anxiogenic side effects for the ligand inhibitors of this invention.

EXAMPLE 14

Automated One-Way Avoidance Learning

The apparatus for both rats and mice is the same as used in passive avoidance testing. It consists of a Skinner box enclosure 48 cm long by 16 cm high by 19 cm deep that contains a grid floor composed of 28 stainless steel bars, 6.3 mm in diameter and spaced 11.7 mm apart for a rat and 62 bars, 3.2 mm in diameter and spaced 5.2 mm apart for a mouse. A 7 watt light and tone generator positioned at each end of the box serve as conditioned stimuli. The position of the animal is detected by breakage of an array of sixteen photobeams spaced at 3.3 cm intervals just above the grid floor.

To begin a training session, a rat or mouse is placed at the end of the footshock compartment, facing away from the door. On Trial 1 only, the door is left closed for 10 sec, then opened and footshock is administered simultaneously. This makes the first trial an escape-only trial, ensuring that the animal does not avoid shock by entering the safe compartment through spontaneous exploration. The footshock continues until the animal escapes or until 20 sec (for mice) or 30 sec (for rats) have elapsed. As soon as the animal enters the safe compartment with all four paws, the door is closed and the inter-trial interval is begun. If an animal does not escape the shock before it is turned off, it is coaxed through the door into the safe compartment, then the door is closed and the inter-trial interval is begun.

A 20 sec (for mice) or 30 sec (for rats) inter-trial interval separates the end of one trial from the beginning of the next. During the inter-trial interval, the latency of the subject's response (escape or avoidance) and the number of avoidances made on all trials after the first are recorded. Any response with a latency of less than 10 sec is considered an avoidance. At the end of the inter-trial interval, the subject is placed back in the footshock compartment facing away from the door.

On all trials after the first, the door is opened immediately after placing the subject in the footshock compartment, and the animal is allowed 10 sec to avoid footshock. If an avoidance occurs, the door is shut and the inter-trial interval is immediately initiated. If the subject fails to enter the safe compartment within 10 sec, it receives footshock, which continues until the animal escapes the shock or a maximum of 30 seconds have elapsed. As soon as the animal enters the safe compartment with all four paws, the door is closed and the inter-trial interval begins. If an animal does not escape the shock before it is turned off, it is coaxed the inter-trial interval (return to step 3). This rarely occurs after the first two or three trials. This sequence of steps is repeated for the desired number of trials. Typically, for rats, 8–10 trials are run on the training day and an equal number on the testing day, and for mice, 2–4 trials are run on the training day and 10–14 trials on the testing day.

When employing this strategy, one must take into account the number of avoidances made on the first day. Therefore, the retention score is obtained by subtracting the number of avoidances made during training from those made during testing; higher difference scores are taken to reflect better retention.

The relative capacity of young adult (3 mo old) and aged adult (24 mo old) Brown-Norway rats to acquire and retain a one-way active avoidance response is assessed. Aged rats exhibit fewer avoidance responses during initial acquisition training than young rats. Moreover, the deficit in avoidance learning is sensitive to treatment with a ligand inhibitor of this invention. Performance is significantly improved in aged rats relative to young rats. Moreover, retention is significant at both 1 and 7 days post-acquisition training.

EXAMPLE 15

Automated Passive Avoidance Learning

The apparatus for both rats and mice is the same as used in active avoidance testing (see Example 14).

For the training trial, the animal is placed individually in one compartment of the learning apparatus, which is separated from a second compartment by a guillotine door. Following a three minute habituation period, the door is opened and the latency to enter the second compartment is recorded. When the animal enters with all four paws, the door is closed, and a 0.5 second AC footshock (Coulburn precision shocker) is delivered. After five seconds, the subject is removed and placed in its home cage. At the time of testing (usually 1–7 days later), the animal is returned to the compartment in which it was initially placed for the learning trial, the door is opened and the latency to enter the second compartment is recorded, but the animal is not shocked. Hence, subjects are administered a single 0.5 second shock for the duration of the experiment. The apparatus control and response recording are computer automated (San Diego Instruments, Gemini Avoidance System). The shock stimulator is research grade, precision-regulated equipment which is electrically isolated and overshoot limited for operator and subject safety.

For most strains of rats with weights between 150 and 350 grams, an effective footshock intensity ranges from 0.2–1.0 mA. For most strains of mice with weights between 24 and 35 grams, an effective footshock intensity ranges from 0.15–0.6 mA. The latency time of rats to enter the dark compartment is measured.

Figure 5A:
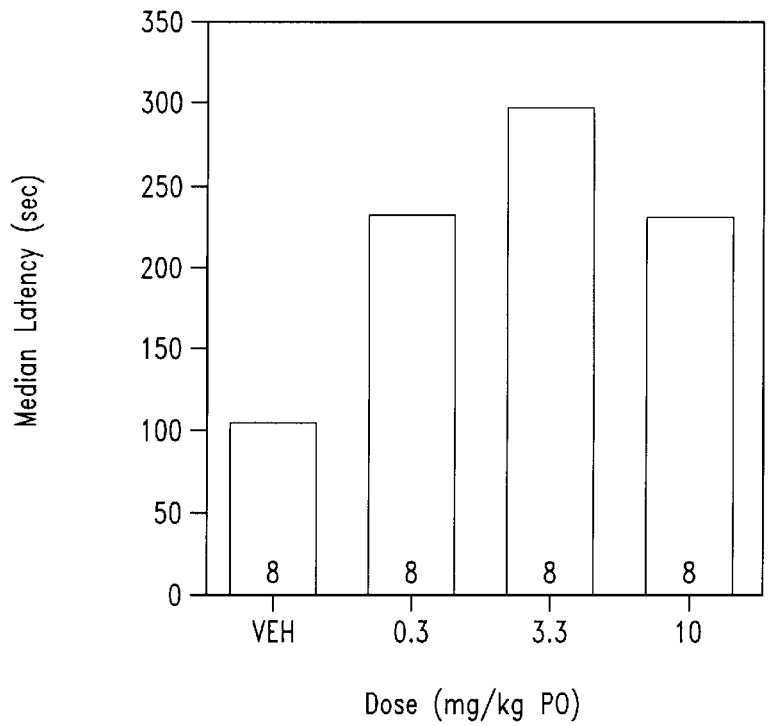
FIGS. 5A and 5B are graphs depicting the effect of administration of representative ligand inhibitors of this invention, Compound Nos. 97-1 and 153, respectively. The ligand inhibitors were administered 5 minutes post-training period in the passive avoidance test.
Figure 5B:
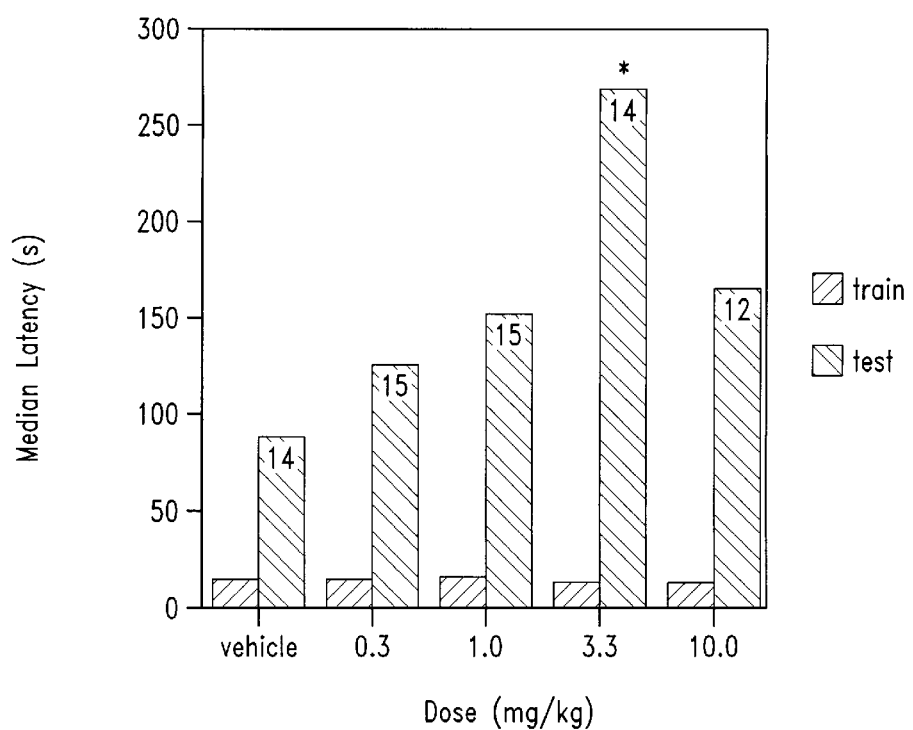

Test Compound Nos. 97-1 and 153 were administered orally 5 minutes after the training period. Both gave an increase in medium latency time to entering the dark compartment. The results of these experiments for Compound Nos. 97-1 and 153 are presented graphically in FIGS. 5A and 5B, respectively.

EXAMPLE 16

Nicotine Withdrawal—Induced Overeating

The effect of ligand inhibitors on overeating is assessed in a model of excessive appetite upon withdrawal of nicotine. Nicotine is administered chronically by subcutaneous implantation of osmotic mini-pumps infusing a solution of nicotine tartrate salt (9 mg/kg/day; 3.15 mg/kg/day nicotine free base) dissolved in saline or saline alone (vehicle). Nicotine withdrawal is achieved by surgical removal of the pump after 14 days.

EXAMPLE 17

Effect of Ligand Inhibition of Zucker Rats

Zucker lean (Fa/?) and obese (fa/fa) rats are treated with vehicle or a ligand inhibitor and food intake or body weight change is measured.

For seven days, baseline measurements are made of the daily food intake and body weight of lean and obese rats. Following these measurements, an osmotic pump-delivering vehicle or the ligand inhibitor is implanted. Ligand inhibitor is delivered at 125 µg/day. The pumps are surgically removed and for the next seven days, daily food intake and body weight measurements are recorded. Rats receiving the ligand inhibitors will show reduced body weight gain or exhibit a body weight loss and ligand inhibitor decreased food intake relative to rats receiving vehicle alone.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A compound having the structure:

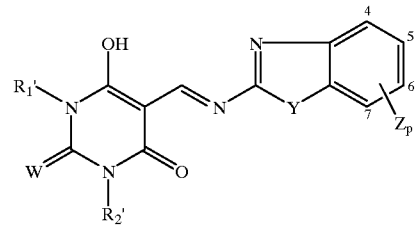

including keto tautomers, stereoisomers and pharmaceutically acceptable acid addition salts thereof, wherein W is selected from S and O;

$R_1'$ and $R_2'$ are the same or different and independently selected from $C_{1-8}$alkyl, $C_{1-8}$alkyloxy$C_{1-8}$alkyl, aryl, substituted aryl, aryl$C_{1-8}$alkyl, substituted aryl$C_{1-8}$alkyl, $C_{3-6}$cycloalkyl, $C_{3-6}$cycloalkyl$C_{1-8}$alkyl, $C_{1-12}$heteroaryl, substituted $C_{1-12}$heteroaryl, $C_{1-12}$heteroaryl$C_{1-8}$alkyl, substituted $C_{1-12}$heteroaryl$C_{1-8}$alkyl, $C_{1-12}$heteroaryl$C_{2-8}$alkenyl and substituted $C_{1-12}$heteroaryl$C_{2-8}$alkenyl;

Y is selected from NH, S, O and N(CH$_3$); and

Z is a substituent, p is 0, 1, 2 or 3 and represents the number of Z substituents, and each occurrence of Z is independently selected from halo, nitro, $C_{1-8}$alkyloxy, $C_{1-8}$alkyl, $C_{2-8}$alkenyl, $C_{2-8}$alkynyl and $C_{1-8}$haloalkyl.

2. The compound of claim 1 wherein W is S.

3. The compound of claim 1 wherein $R_1'=R_2'$.

4. The compound of claim 3 wherein $R_1'$ and $R_2'$ are selected from $C_{1-8}$alkyl, phenyl, benzyl, $C_{1-8}$alkloxy$C_{1-8}$alkyl, phenyl$C_{1-8}$alkyl, substituted phenyl$C_{1-8}$alkyl, furanyl$C_{1-8}$alkyl, and thiophenyl$C_{1-8}$alkyl.

5. The compound of claim 4 wherein $R_1'$ and $R_2'$ are selected from phenyl(CH$_2$)$_3$—, phenyl(CH$_2$)$_2$—, CH$_3$O)(CH$_2$)$_3$—, 3-fluorobenzyl, 3-methoxybenzyl, 3,5-dimethoxybenzyl, thiophenyl-CH$_2$—, furanyl-CH$_2$— and $C_{1-8}$alkyl.

6. The compound of claim 1 wherein Y is selected from —S— and —NH—.

7. The compound of claim 6 wherein p is 0.

8. The compound of claim 6 wherein p is 1.

9. The compound of claim 8 wherein Z is chloro attached at position 5 or 6.

10. The compound of claim 8 wherein Z is methyl attached at position 4, 5 or 6.

11. The compound of claim 8 wherein Z is methoxy attached at position 4, 5 or 6.

12. The compound of claim 8 wherein Z is nitro attached at position 6.

13. The compound of claim 6 wherein p is 2.

14. The compound of claim 13 wherein Z is methyl attached at positions 5 and 6.

15. The compound of claim 13 wherein Z is chloro attached at positions 5 and 6.

16. The compound of claim 1 wherein W is S, $R_1'=R_2'$, p is 2, and Z is methyl attached at positions 5 and 6.

17. The compound of claim 1 wherein W is S, $R_1'=R_2'$, p is 1, and Z is methoxy attached at position 5.

18. The compound of claim 1 wherein W is S, $R_1'=R_2'$, p is 1, and Z is methyl attached at position 5.

\* \* \* \* \*